US010842509B2

(12) United States Patent
Little et al.

(10) Patent No.: US 10,842,509 B2
(45) Date of Patent: Nov. 24, 2020

(54) ORTHOPAEDIC DEVICE FOR CORRECTION OF DEFORMITIES IN A BONE

(71) Applicant: The Sydney Children's Hospitals Network (Randwick and Westmead), West Mead (AU)

(72) Inventors: David Graham Little, West Pennant Hills (AU); Irene Yang, Cremorne (AU); Tegan Cheng, Alexandria (AU)

(73) Assignee: The Sydney Children's Hospitals Network (Randwick and Westmead)

( * ) Notice: Subject to any disclaimer, the term of this patent is extended or adjusted under 35 U.S.C. 154(b) by 250 days.

(21) Appl. No.: 15/548,330

(22) PCT Filed: Feb. 4, 2016

(86) PCT No.: PCT/AU2016/050064
§ 371 (c)(1),
(2) Date: Aug. 2, 2017

(87) PCT Pub. No.: WO2016/123671
PCT Pub. Date: Aug. 11, 2016

(65) Prior Publication Data
US 2018/0021050 A1    Jan. 25, 2018

(30) Foreign Application Priority Data

Feb. 5, 2015  (AU) .................................. 2015900355
Jul. 1, 2015   (AU) .................................. 2015902575
Oct. 13, 2015 (AU) .................................. 2015904155

(51) Int. Cl.
*A61B 17/17* (2006.01)
*A61B 17/80* (2006.01)

(52) U.S. Cl.
CPC .......... *A61B 17/1728* (2013.01); *A61B 17/80* (2013.01); *A61B 17/809* (2013.01); *A61B 17/8057* (2013.01); *A61B 17/8085* (2013.01)

(58) Field of Classification Search
CPC ... A61B 17/1728; A61B 17/80; A61B 17/809; A61B 17/8085; A61B 17/8057
See application file for complete search history.

(56) References Cited

U.S. PATENT DOCUMENTS

| 5,395,372 A | 3/1995 | Hold et al. |
| 6,022,350 A | 2/2000 | Ganem |

(Continued)

FOREIGN PATENT DOCUMENTS

| WO | 2000044293 | 8/2000 |
| WO | 2006122194 | 11/2006 |

(Continued)

OTHER PUBLICATIONS

WIPO, PCT/AU2016/050064, IPRP, 12 pgs. dated Aug. 8, 2017.
AIPO, PCT/AU2016/050064, Search Report & Written Opinion, 20 pgs. dated Mar. 16, 2016.

*Primary Examiner* — Christopher J Beccia
(74) *Attorney, Agent, or Firm* — John V. Daniluck; Dentons Bingham Greenebaum LLP

(57) ABSTRACT

An orthopaedic device for correcting deformities in a bone is disclosed, the device including first and second end portions to fix to first and second bone regions either side of a growth plate, and a connection portion extending between the first and second end portions. At least the first end portion can protrude relative to the connection portion such that it is at least partly receivable in a first recess formed in the first bone region. The first end portion can be in the form of an end cup and can be fixed to the first bone region by a fixation device such as a screw. A head of the screw can sit (Continued)

within the end cup. The second end portion can be similar to the first end portion or alternatively may comprise a hook, blade or staple.

35 Claims, 19 Drawing Sheets

(56) References Cited

U.S. PATENT DOCUMENTS

| | | | |
|---|---|---|---|
| 2004/0111089 A1* | 6/2004 | Stevens | A61B 17/1728 606/86 B |
| 2009/0030518 A1 | 1/2009 | Aubin et al. | |
| 2010/0004691 A1* | 1/2010 | Amato | A61B 17/1728 606/280 |
| 2011/0137351 A1* | 6/2011 | Huebner | A61B 17/8052 606/286 |
| 2013/0046314 A1 | 2/2013 | Trimed | |

FOREIGN PATENT DOCUMENTS

| | | |
|---|---|---|
| WO | 2013130978 | 9/2013 |
| WO | 2014161533 | 10/2014 |

* cited by examiner

ORTHOPAEDIC DEVICE FOR CORRECTION OF DEFORMITIES IN A BONE

CROSS-REFERENCE TO RELATED APPLICATIONS

This application is a national stage filing of international patent application no. PCT/AU2016/050064 filed 4 Feb. 2016, which claims priority from Australian provisional patent application no. 2015900355 filed 5 Feb. 2015, from Australian provisional patent application no. 2015902575 filed 1 Jul. 2015, and from Australian provisional patent application no. 2015904155 filed 13 Oct. 2015, the contents of each of these application being incorporated herein by reference.

TECHNICAL FIELD

The present disclosure relates to orthopaedic devices for correction of deformities in a bone, including deformities in bones at or adjacent a growth plate.

BACKGROUND

A growth plate, also known as the epiphyseal plate or physis, is a growing area of tissue in the metaphysis at each end of a bone such as a long bone or vertebra. The growth plate determines the future length and shape of the mature bone. The plate is found in growing children and adolescents. When growth is complete, the growth plate closes and is replaced by an epiphyseal line of solid bone.

Growth plates are commonly the weakest areas of the growing skeleton, being weaker than nearby ligaments and tendons that connect to other bones and muscles. Growth plates are therefore vulnerable to injury and specifically fractures.

In some children, a growth plate will grow non-uniformly, with growth on one side of the growth plate being faster than on another side of the growth plate, causing an angular or rotational deformity of the bone. Angular or rotational deformity of the bone can also result from trauma at or away from the growth plate, from a bone, cartilage or metabolic disorder, or can be congenital. Traditional methods of treating such deformities include insertion of staples, k-wires, or screws into the growth plate to restrain or temporarily arrest growth on one side of the growth plate while allowing the other side to grow and correct the angular deformity. In some instances, however, the restricted side of the growth plate may fuse closed while the other side of the growth plate is still growing, thereby resulting in an over-correction of the angular deformity, resulting in an angular deformity in an opposite direction.

"Guided growth" is a term used to describe manipulation of bone growth in children. The term infers that some deformity is present, and that correction can be achieved by altering the way the bone grows. The first widely adopted guided growth technique was the use of staples for hemi-epiphysiodesis, principally around the knee to correct genu varum (bow legs) and genu valgum (knock knees). Blount described the use of stapling for the correction of leg length discrepancy as well as stating that "Angular deformity may be corrected during the growth period. Knock-knee, bowleg, back-knee, flexion deformity, or combinations of these deformities are rapidly overcome" (Blount W P, Clarke G R. *Control of bone growth by epiphyseal stapling; a preliminary report*). Subsequent reports illustrated that although feasible, the force of the growth plate would open the staple and often force it to back out of the bone.

Screws have also been used to asymmetrically tether growth, particularly at the ankle to control ankle valgus (Stevens P M, Belle R M. *Screw epiphysiodesis for ankle valgus. J Pediatr Orthop.* 1997 January-February; 17(1):9-12). Stevens is credited with the introduction of plates and screws to achieve guided growth instead of staples, resulting in the development of a tension band plate for guided growth known as the Eight-Plate™, and which is described in US Patent Application Publication No. US20040111089 A1. Tension band plates and screws do not usually back out of the bone, lessening this complication associated with stapling. A commercially available Eight-Plate™ is made from titanium (Orthofix). Other commercially available tension band plates for guided growth are made from stainless steel and include the PediPlates™ (OrthoPediatrics) and the Hinge Pediatric Plating System™ (Pega Medical).

Tension band plate and screw constructs for guided growth sit externally to the perichondrial ring of the growth plate and can be prominent relative to the bone. The constructs can cause significant irritation to the recipient and/or decrease a range of motion of the patient's limbs.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to one aspect, the present disclosure provides an orthopaedic device for fixing between first and second regions of bone separated by a growth plate, the orthopaedic device comprising:

a first end portion to fix to the first bone region;

a second end portion to fix to the second bone region; and a connection portion connected between the first and second end portions to extend across an outer surface of the bone between the first and second bone regions, wherein, at least the first end portion protrudes relative to the connection portion such that it is at least partly receivable in a first recess formed in the first bone region, and wherein the first end portion defines a first opening to receive a first fixation device to fix the orthopaedic device to the first bone region.

In one embodiment, the second end portion also protrudes relative to the connection portion such that it is at least partly receivable in a second recess formed in the second bone region.

In one embodiment, the second end portion defines a second opening to receive a second fixation device to fix the orthopaedic device to the second bone region.

Alternatively, the second end portion may not define any opening to receive a second fixation device. The second end portion may not be fixed to the second bone region using a second fixation device. Instead, for example, the second end portion may be fixed to the second bone region through use of a hook, staple, blade or other engagement feature that may be comprised in the second end portion.

When the first and second end portions are fixed to the first and second bone regions, the connection portion may extend across an outer surface of the bone, including the growth plate, to fix the first and second regions of bone together, preventing or limiting growth of the growth plate adjacent the first and second bone regions. In this regard, the device may form part of a guided growth system or otherwise. The device may provide a tension band plate for guided growth, for example.

According to one aspect, the present disclosure provides a method of guiding growth of a bone, the bone including first and second regions of bone separated by a growth plate, the method comprising:

locating a first end portion of an orthopaedic device in a first recess at the first bone region; and locating a second end portion of the orthopaedic device at the second bone region;

wherein the orthopaedic device has a connection portion connected between the first and second end portions, and wherein, the first end portion protrudes relative to the connection portion such that the connection portion extends across an outer surface of the bone between the first and second bone regions when the first end portion is located in the first recess and the second end portion is located at the second bone region, and wherein the first end portion defines a first opening to receive a first fixation device and the method comprises fixing the first end portion to the first bone region by extending the first fixation device through the first opening and into the first bone region.

In one embodiment, the method comprises locating the second end portion in a second recess at the second bone region, wherein the second end portion also protrudes relative to the connection portion. The second end portion may define a second opening to receive a second fixation device and the method may comprise fixing the second end portion to the second bone region by extending the second fixation device through the second opening and into the second bone region.

Alternatively, the second end portion may not define any opening to receive a second fixation device. The second end portion may not be fixed to the second bone region using a second fixation device. Instead, for example, the second end portion may be fixed to the second bone region by engaging a hook, staple, blade or other feature that may be comprised in the second end portion, with the second bone region.

In any aspects disclosed herein, the connection portion may be a substantially planar element. The connection portion may be flat or may have a gently curving shape or otherwise. In general, the connection portion may sit on top of and remain prominent at the outer surface of the bone. Meanwhile, through their protrusion relative to the connection portion, the first and/or second end portions can be at least partly received in the respective recesses formed in the bone. The first and/or second end portions can be at least partly concealed or buried in the bone while the connection portion extends across the outer surface of bone. The first and/or second end portions may be considered as countersunk or counterbored within the bone. In this regard, the recesses formed in the bone may considered as countersinks or counterbores. By concealing, burying, counterboring and/or counterskinking the first and/or second end portions at least partially in the bone, the overall device can have a reduced prominence at the outer surface of the bone. This can reduce the potential for the device to cause irritation to the recipient and the potential for the device to limit motion of the patient's limbs, for example.

When the first and second end portions are fixed to the first and second bone regions, an inner (or bottom) surface of the connection portion may face in an inwards direction towards the outer surface of the bone, and an outer (or top) surface of the connection portion may face in an outwards direct away from the outer surface of the bone. Similarly, an inner surface of each of the first and second end portions may face towards the outer surface of the bone, including walls defining recesses in the outer surface of the bone.

The first end portion, or both the first and second end portions, may protrude relative to the connection portion in the inward direction. The first end portion, or both the first and second end portions, may be considered to protrude below the connection portion. The protrusion of the first and second end portions relative to the connection portion may be such that a shoulder region is formed at an interface between an inner surface of each of the first and second end portions and an inner surface of the connection portion. In particular, a first shoulder region may be formed between the inner surface of the first end portion and the inner surface of the connection portion at a first end of the connection portion, and a second shoulder region may be formed between the inner surface of the second end portion and the inner surface of the connection portion at a second end of the connection portion. The shoulder regions may define an angle of at least 60 degrees, at least 70 degrees, at least 80 degrees, at least 90 degrees, at least 100 degrees or higher.

The first and/or second fixation device may be a bone screw. Each bone screw may have a threaded shaft and a head. The head may abut an outer surface of each end portion surrounding the respective opening, while the threaded shaft may extend through the opening in the inward direction towards the bone.

One or both of the first and second end portions may be a cup. The opening in the end portion may extend through a bottom wall of the cup. The bottom wall may be surrounded by side walls, e.g. cylindrical side walls, of the cup. The head of the bone screw may partially or entirely locate within the cup.

In some embodiments, each end portion may have a size and shape that permits pivotal rotation of the fixation device, e.g. bone screw, relative to the orthopaedic device, upon growth of bone adjacent to the bone screws. Where two bone screws are provided, for example, each bone screw may rotate in this manner. In alternative embodiments, however, it can be desirable to restrict pivotal rotation of one of the two bone screws, for example. It has been found that pivotal rotation of a bone screw fixed to the epiphysis may in some circumstances cause shifting of the orthopaedic device relative to the surface of the bone to a position where it may interfere with and potentially cause damage to the growth plate. To prevent this, pivotal rotation of one of the bone screws relative to the device may be restricted, e.g., using a locking mechanism. The locking mechanism may lock the head of the bone screw to the second end portion, for example. In one embodiment, the locking mechanism comprises a threaded engagement between a head of the bone screw and the second end portion, for example.

According to one aspect, the present disclosure provides an orthopaedic device for fixing between first and second regions of bone separated by a growth plate, the orthopaedic device comprising:

a first end portion to fix to the first bone region;

a second end portion to fix to the second bone region; and a connection portion connected between the first and second end portions to extend across an outer surface of the bone between the first and second bone regions, wherein, the first end portion defines a first opening to receive a first fixation device to fix the orthopaedic device to the first bone region;

wherein, the second end portion defines a second opening to receive a second fixation device to fix the orthopaedic device to the second bone region;

wherein the first end portion is configured to allow pivotal rotation of the first fixation device relative to the orthopaedic device when the first fixation device is received in the first end portion; and wherein the second end portion is configured to prevent pivotal rotation of the second fixation device relative to the orthopaedic device when the second fixation device is received in the second end portion.

The second end portion may comprise a locking mechanism to prevent pivotal rotation of the second fixation device. The locking mechanism may comprise a screw thread surrounding an opening in the second end portion, the opening adapted to receive a shaft of the second fixation device, e.g. bone screw, therethrough. The head of the bone screw may comprise a complimentary screw thread for threadedly engaging the screw thread of the second end portion. Alternative locking mechanisms may be provided, however, including additional fixation devices, e.g. locking screws, that fix the position of the head of the bone screw in the second end portion.

The terms "first end portion", "second end portion", "first end cup" and "second end cup" are used herein to describe specific portions of the orthopaedic device located at either side of a connection portion. The use of the word "end" in this context should not be construed as limiting these specific portions of the orthopaedic devices to location at edges or terminal ends of the device. It is conceived that further elements may be connected to the first and second end portions or first and second end cups, for example.

In aspects disclosed herein, one of the first and second bone regions may be the epiphysis and the other of the first and second bone regions may be the metaphysis. For example, in one embodiment, the first bone region is the metaphysis and the second bone region is the epiphysis.

The first and second bone regions may be any bone regions separated by at least one growth plate. The first and second bone regions may be part of the same bone or may be located in different bones. As one example, the first and second bone regions may be part of one or more long bones such as a femur, tibia, fibula, humerus, ulna, radius, phalange, metacarpal, metatarsal or otherwise. As another example, the first and second bone regions may be part of one or more irregular bones such as vertebrae of the spine. As one example, the first bone region may be part of a first vertebra and the second bone region may be part of a second vertebra. The first and second vertebrae may be adjacent one another. The first end portion may to fix to the first vertebra, the second end portion may fix to the second vertebra and the connection portion may extend across an outer surface of the vertebrae and across a vertebral disc located between the vertebrae. The connection portion may extend across two growth plates, one from each of the vertebrae.

In accordance with discussions above, in one aspect, the present disclosure provides an orthopaedic device for fixing between first and second regions of bone separated by a growth plate, the orthopaedic device comprising:

a first end cup including an opening to receive a first bone screw;

a second end cup including an opening to receive a second bone screw; and a connection portion connected between the first and second end cups, wherein at least one of the first and second end cups protrudes below a bottom surface of the connection portion.

In this aspect, the first end cup, second end cup and/or connection portion may have any one of more the features herein described with respect to other aspects. For example, the end cups may include openings, e.g. elongated openings, through which a shaft of a bone screw may extend to secure the end cups to the bone.

In any aspect described herein, the device may take a neutral (balanced) configuration. In this regard, the device may be substantially symmetrical either side of a midpoint of the connection portion, the midpoint being halfway along the connection portion between the first and second end portions. In the neutral configuration, both the first and second shoulder regions of the device may define substantially the same angle. The first and second end portions may therefore protrude relative to the inner surface of the connection portion, at the first and second ends of the connection portion, respectively, at substantially the same angle. The same angle may be approximately at least 60 degrees, at least 70 degrees, at least 80 degrees, at least 90 degrees, at least 100 degrees or higher.

Alternatively, the device may have an offset (unbalanced) configuration. In this regard, the device may have a non-symmetrical shape either side of the midpoint of the connection portion. In the offset configuration, the first and second shoulder regions of the device may define different angles. The first and second end portions may therefore protrude relative to the inner surface of the connection portion, at the first and second ends of the connection portion, respectively, at different angles. The angles may be different by at least 10 degrees, at least 20 degrees, at least 30 degrees or otherwise. For example, the first shoulder region may define an angle of approximately 90 degrees and the second shoulder region may define an angle of approximately 130 degrees, or vice versa.

The neutral or offset configurations may enable the device to be used with bones having different outer surface profiles. For example, where the first and second regions of the bone either side of the growth plate have a relatively symmetrical outer profile, the device with a neutral configuration may be used. On the other hand, where the first and second regions of the bone either side of the growth plate have an asymmetrical outer surface profile, the device with an offset configuration may be used.

Whether or not the plate takes a neutral or offset configuration, the first and second end portions may protrude along respective first and second axes that are parallel to each other. The first and second axes may extend in an inward direction centrally through the cups. Bone screws extending through the cups may align along the first and second axes substantially parallel to each other. Nevertheless, upon implantation or only following post-implantation bone growth, the bone screws may be angled relative to each other and/or the first and second axes. To enable the bone screws to extend through openings in the end portions at different angles, the openings may be elongated.

One or more of the bone screws used with the device may be solid screws. Additionally or alternatively, one or more of the bone screws may be cannulated (e.g., they may contain a central bore) so they may be extended over a guide member such as a guide wire in order to be inserted into openings in the device. To advance the cannulated bone screws, a cannulated screwdriver may be used. The guide member may be subsequently removed.

The orthopaedic device may be formed in one-piece. Material forming the orthopaedic device may be homogeneous or inhomogeneous. For example, the orthopaedic device may be formed in one-piece of a surgical grade metal, e.g., cobalt chromium alloy, titanium or stainless steel, formed in one-piece of a polymer such as PEEK, or formed in one-piece of carbon fibre.

The orthopaedic device may be formed in more than one piece. The end portions may be formed of different material from the connection portion. The end portions may be rigid and the connection portion may be non-rigid, for example. Where the connection portion is non-rigid, the connection portion may exhibit strength under tension but not under compression, for example. The connection portion may comprise a flexible link. The flexible link may be a flexible tape, e.g. a flexible elongate piece or band of material. The flexible material may be formed of a woven mesh or otherwise. The flexible material may comprise any one or more of polyester, polyethylene terephthalate (PET), polypropylene and polytetrafluoroethylene. Materials suited for use in artificial ligaments may be used, for example. The connection portion, and indeed the end portions, may be non-resorbable, non-degradable and biocompatible. The end portions may be formed of a surgical grade metal, e.g., cobalt chromium alloy, titanium or stainless steel, of a polymer such as PEEK, or of carbon fibre, for example.

When the connection portion comprises a flexible link such as a flexible tape, the flexible link may connect to the first and/or second end portions by extending into slots provided in the end portions. Alternative means to connect the flexible link to the end portions may be provided, however, including fixation means such as screws, adhesive or otherwise.

According to one aspect, the present disclosure provides an orthopaedic device for fixing between first and second regions of bone separated by a growth plate, the orthopaedic device comprising:

a first end portion to fix to the first bone region;
a second end portion to fix to the second bone region; and
a connection portion connected between the first and second end portions to extend across an outer surface of the bone between the first and second bone regions,
wherein, the first and second end portions are substantially rigid and the connection portion is non-rigid.

In this aspect, the first end portion, second end portion and/or the connection portion may be configured as described above with respect to preceding aspects. For example, the connection portion may comprise a flexible link. The flexible link may be a flexible tape, e.g. a flexible elongate piece or band of material. The flexible material may be formed of a woven mesh or otherwise. The connection portion may connect to the first and/or second end portions by the flexible link extending into slots provided in the end portions. Alternative means to connect the flexile link to the end portions may be provided, however, including fixation means such as screws, adhesive or otherwise. The first and second end portions may be cups having openings to receive bone screws.

In this aspect, as for previous aspects, one or both first and second end portions may protrude relative to the connection portion such that they are at least partly receivable in a respective recess formed in the bone. However, it is recognised that, alternatively, the first and second end portions may substantially not protrude relative to the connection portion and may not be designed for receipt in recesses formed in the bone. Advantages may be achieved through use of a non-rigid connection portion in combination with substantially rigid first and second end portions that have a variety of different configurations. The orthopaedic device may be adapted for use with bone having a variety of different surface profiles. The connection portion may flex or bend in order to adapt to the different surface profiles, while the device may still provide considerable strength under tension for use in guided growth or otherwise.

In aspects described above, an orthopaedic device is described that includes first and second end portions wherein, in some embodiments, the second end portion is configured in substantially the same manner as the first end portion. For example, both the first and second end portions may protrude in the same direction relative to the connection portion for receipt in respective first and second recesses. Both the first and second end portions may be in the form of cups that include openings, for example. Nevertheless, as also indicated above, the second end portion may be configured differently from the first end portion. For example, while the second end portion may also protrude relative to the connection portion, it may protrude in a different direction. Additionally or alternatively, the second end portion may not be configured to receive a respective fixation device.

In one embodiment, the second end portion comprises a hook. The hook may be adapted to hook around a portion of the second bone region to connect the second end portion to the second bone region. The hook may be adapted to at least partially locate in a second recess formed in the second bone region or locate around a native outer surface of the second bone region only. Where a second recess is provided, a distal end portion of the hook may be located in the second recess, for example. The second recess may be located on a second bone surface that is at an angle to a first surface bone surface in which the first recess is located. The first and second surfaces may be at an angle relative to each other of at least 45 degrees, at least 60 degrees, at least 75 degrees or about 90 degrees.

The hook may extend from the second end of the connection portion and bend at an angle relative to the connection portion of at least 90 degrees, at least 120 degrees, at least 150 degrees or about 180 degrees.

The hook may comprise first and second opposing surfaces. The hook may be formed from a plate that is bent or cast into a hook shape. The plate may also form part of the connection portion. The first and second opposing surfaces of the hook may each taper in width towards a distal end of the hook. The hook may therefore be narrower towards its distal end, enabling receipt of a distal end portion of the hook in a relatively small second recess. Additionally or alternatively, the distal end portion of the hook may comprise two or more prongs for receipt in respective second recesses. Multiple second recesses may therefore be provided, of relatively small size, without necessarily requiring tapering of the hook to engage therewith.

In another embodiment, the second end portion comprises a staple. The staple may comprise at least two prongs. The two prongs may extend substantially parallel to each other. Each prong may be substantially straight. Each prong may taper towards its distal end. The prongs of the staple may be adapted to project into respective second recesses formed in the second bone region.

The prongs of the staple may extend from the second end of the connection portion at an angle relative to the connection portion of about 60 to 120 degrees, for example. The staple may be formed from a plate that is bent or cast to provide the staple shape. The plate may also form part of the connection portion.

In another embodiment, the second end portion comprises a blade. The blade may be adapted to project into a respective second recess formed in the second bone region. The blade may extend from the second end of the connection portion at an angle relative to the connection portion of about 60 to 120 degrees, for example. The blade may be formed from a plate that is bent or cast to provide the blade shape. The plate may also form part of the connection portion.

A hook, staple or blade may be employed at the second end portion when, for example, there is insufficient space at the second bone region for the second bone region to receive a second end cup and/or a second bone fixation device. The hook, staple or blade may provide a less invasive means of fixation to the second end portion. When a hook, staple or blade is used to fix to the second bone region, the second bone region may be specifically the epiphysis, with the first bone region being the metaphysis. In general, since the epiphysis is located at the end of a bone such as a long bone, a hook may be particularly suited to hooking around a portion of the epiphysis. Moreover, the epiphysis is generally smaller than the metaphysis, so is more likely to have insufficient space to receive a second end cup and/or second bone fixation device, which may be larger than a hook, staple or blade. Further, it may be considered undesirable by some users to form a recess in articular cartilage at the epiphysis to receive any second end cup. Forming one or more relatively small recesses to receive a hook, staple or blade may be preferred by a user in certain circumstances. Even though it may be preferable to use a second end portion comprising a hook, staple or blade in conjunction with the epiphysis, a first end portion comprising a hook, blade or staple may be used in conjunction with the metaphysis in some embodiments.

According to one aspect, the present disclosure provides an orthopaedic device for fixing between first and second regions of bone separated by a growth plate, the orthopaedic device comprising:

a first end portion to fix to the first bone region;

a second end portion to fix to the second bone region; and a connection portion connected between the first and second end portions to extend across an outer surface of the bone between the first and second bone regions, wherein the first end portion defines a first opening to receive a first fixation device to fix the orthopaedic device to the first bone region; and wherein the second end portion comprises a hook, a staple or a blade to extend into one or more recesses in the second bone region to fix the orthopaedic device to the second bone region.

In some embodiments, the first end portion may in the form of a first end cup, for example, and may protrude relative to the connection portion such that it is at least partly receivable in a first recess formed in the first bone region, in accordance with discussions further above. However, in alternative embodiments, the first end portion may not protrude relative to the connection portion. The first opening of the first end portion may be comprised in a relatively flat plate member, for example.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments of the present disclosure are now described with reference to the accompanying drawings in which.

DESCRIPTION OF EMBODIMENTS

Figure 1A:
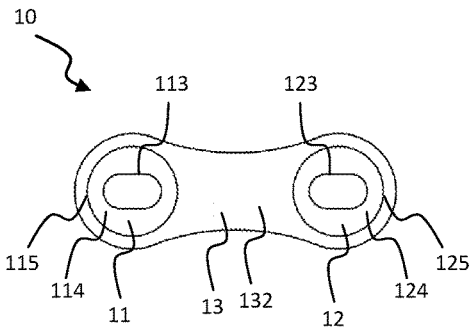
FIGS. 1a to 1d show a top plan view, top oblique view, enlarged lateral view, and bottom oblique view, respectively, of an orthopaedic device according to an embodiment of the present disclosure.
Figure 1B:
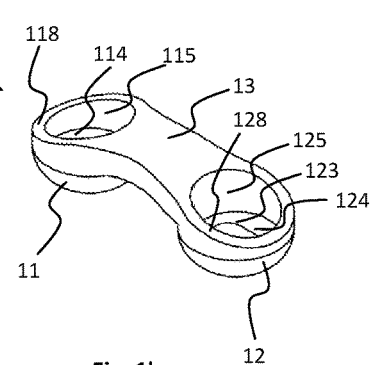

An orthopaedic device 10 according to an embodiment of the present disclosure is illustrated in FIGS. 1a to 1d. A cross-sectional view of the device 10 implanted at a bone, specifically the end of a long bone, is illustrated in FIG. 1e. The device 10 can fix together first and second regions of bone 101, 102 separated by a growth plate 103. The device 10 includes a first end portion in the form of a first end cup 11, to fix to the first bone region 101, and a second end portion in the form of a second end cup 12, to fix to the second bone region 102. A connection portion 13 is connected between the first and second end cups 11, 12. When the first and second end cups 11, 12 are fixed to the first and second bone regions 101, 102, the connection portion 13 can extend across an outer surface 100 of the bone, including an outer surface of the growth plate 103, between the first and second bone regions 101, 102. Therefore, when the first and second end cups 11, 12 are fixed to the first and second bone regions 101, 102, the first and second regions of bone 101, 102 can be linked together, preventing or limiting growth of the growth plate 103 at a region therebetween. In this regard, the orthopaedic device 10 may be used in a guided growth system that corrects deformities in the bone by altering the way the bone grows. The orthopaedic device 10 may provide a tension band plate for guided growth, for example.

In the present embodiment, the orthopaedic device 10 is formed in one-piece from surgical grade metal, e.g., cobalt chromium alloy or titanium. However, alternative materials may be used and/or the device 10 may be formed from multiple pieces.

The connection portion 13 is a substantially planar element with a gentle curvature such that it arches slightly away from the outer surface 100 of the bone, providing a form of bridge or bridging element. The connection portion 13 is adapted to extend across and remain prominent at the outer surface 100 of the bone. The connection portion includes an inner (or bottom) surface 131 on one side and an outer (or top) surface 132 on an opposite side. When the first and second end cups 11, 12 are fixed to the first and second bone regions 101, 102, the inner surface 131 is configured to face in an inwards direction towards the outer surface 100 of the bone. In some instances, the inner surface 131 may abut the outer surface 100 of the bone.

Similarly, inner surfaces 111, 121 of each of the first and second end cups 11, 12 are configured to face towards the bone. The first and second end cups 11, 12 each protrude inwardly of the inner surface 131 of the connection portion 13. The arrangement is such that, when the connection portion 13 extends across the outer surface 100 of the bone, the first and second end cups 11, 12 can protrude into first and second recesses 104, 105, respectively, that are formed in the first and second bone regions 101, 102. The first and second recesses 104, 105 may be formed through drilling or other techniques, as described further below. Thus, the first and/or second end cups 11, 12 can be at least partly concealed or buried in the bone, ensuring that the ends of the device 10 have reduced prominence at the outer surface 100 of the bone, reducing the potential for the device 10 to cause irritation to the recipient and/or the potential for the device 10 to reduce a range of motion of a limb of the patient. The first and second recesses 104, 105 can be counterbores that receive the first and second end cups.

Figure 1C:
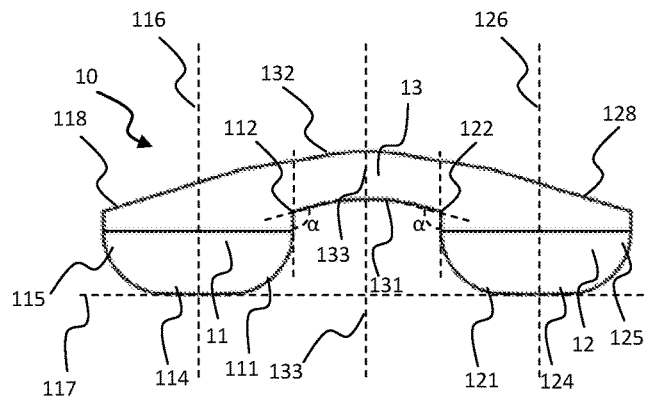
Figure 1D:
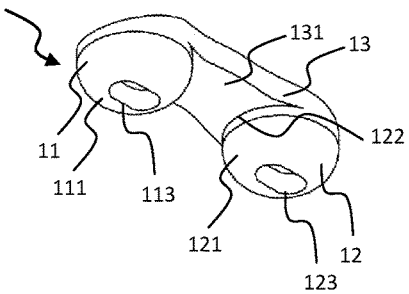
Figure 1E:
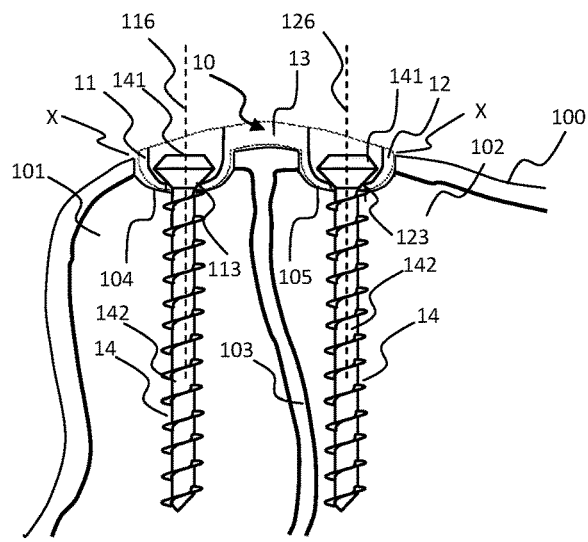
FIG. 1e shows a cross-sectional view of the device of FIGS. 1a to 1d implanted at a bone.
Figure 2A:
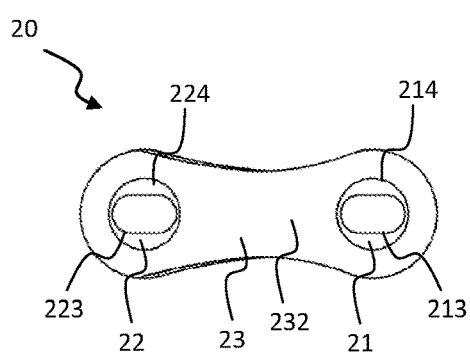
FIGS. 2a to 2d show a top plan view, top oblique view, enlarged lateral view, and bottom oblique view, respectively, of an orthopaedic device according to another embodiment of the present disclosure.
Figure 2B:
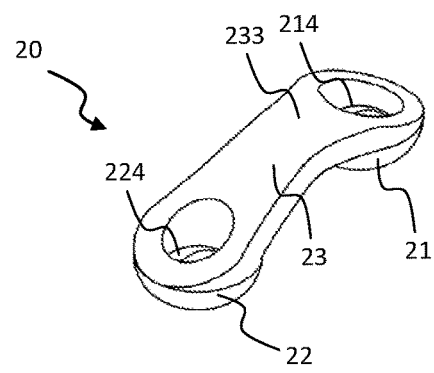
Figure 2C:
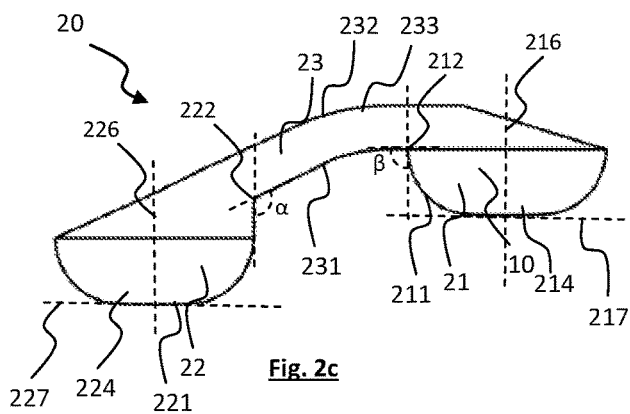
Figure 2D:
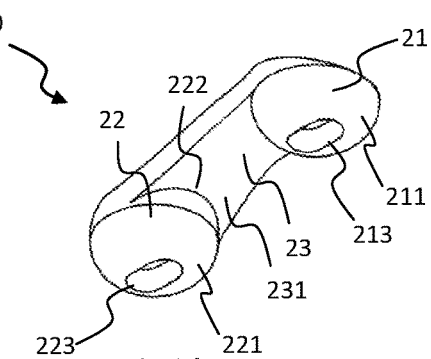

As best seen in FIG. 1c, the protrusion of the first and second end cups 11, 12 relative to the connection portion 13 is such that shoulder regions 112, 122 are formed at interfaces between the inner surfaces 111, 121 of the first and second end cups 11, 12 and the inner surface 131 of the connection portion 13. In particular, a first shoulder region 112 is formed at the interface between the inner surface 111 of the first end cup 11 and the inner surface 131 of the connection portion 13 at a first end of the connection portion 13, and a second shoulder region 122 is formed between the inner surface 121 of the second end cup 12 and the inner surface 131 of the connection portion 13 at a second end of the connection portion 13. In this embodiment, the first and second shoulder regions 112, 122 each define an angle α of about 100 degrees.

A bottom wall 114, 124 of each of the first and second end cups 11, 12 defines an opening 113, 123 to receive a fixation device such as a bone screw 14, as illustrated in FIG. 1e, for example. The bottom wall 114, 124 of each cup 11, 12 is surrounded by cylindrical side walls 115, 125 that project in an outward (upward) direction from edges of the bottom wall 114, 124. Each bone screw 14 includes a head 141 and a threaded shaft 142 extending from the head 141. The screw head 141 can abut an outer surface of the bottom wall 114, 124 of the cup 11, 12, while the threaded shaft 142 extends through the opening 113, 123 and into the bone to fix the end cup 11, 12 to the bone. The head 141 of each bone screw is entirely locatable within the respective end cup 11, 12 such that the head 141 does not protrude from the orthopaedic device 10 and such that the head 141 can also be located within the respective recess 104, 105 when the end cup 11, 12 is located in the recess 104, 105.

The orthopaedic device 10 illustrated in FIGS. 1a to 1e takes a neutral (or balanced) configuration. In this regard, the device 10 is substantially symmetrical either side of a midpoint 133 of the connection portion 13, the midpoint 133 being halfway along the connection portion between the first and second end cups 11, 12 as illustrated in FIG. 1c. This symmetry is achieved in part through the first and second shoulder regions 112, 122 of the device 10 defining substantially the same angle α as discussed above, meaning that the first and second end cups 11, 12 protrude relative to the respective, immediately adjacent, regions of the inner surface 131 of the connection portion 13, at substantially the same angle. In the neutral configuration, the bottom walls 114, 124 of the end cups 11, 12 extend across the same plane 117.

The first and second end cups 11, 12 protrude along respective first and second axes 116, 126 that are parallel to each other. The first and second axes 116, 126 extend centrally through the cups 11, 12 and through the openings 113, 123 in the cups 11, 12. By having the first and second end cups 11, 12 protruding along parallel axes 116, 126, the first and second end cups 11, 12 can be simultaneously inserted into the recesses 104, 105, the recesses being shaped and sized similarly or substantially identically to the end cups 11, 12. The bone screws 14 extending through the cups 11, 12 can align along the first and second axes 116, 126 substantially parallel to each other as shown in FIG. 1e. Nevertheless, as the bone grows, the bone screws 14 may rotate (pivot) and therefore take up different angles relative to the first and second axes 116, 126. To enable the bone screws to take up different angles, the openings 113, 123 in the cups 11, 12 are elongated.

Outer (or top) surfaces 118, 128 of the end cups 11, 12 are angled relative to the bottom walls 114, 124 of the end cups 11, 12. The side walls 115, 125 of the end cups 11, 12 are deeper towards the centre of the orthopaedic device 10 and shallower towards the adjacent edge of the orthopaedic device 10, along an axis of elongation of the device between the first and second end cups 11, 12. The arrangement is such that the orthopaedic device 10 has a shallower profile towards the edges of the device 10 in the axis of elongation. Steps between the outer surfaces 118, 128 of the end cups and the outer surface 100 of the bone at these edges of the device 10 can therefore be reduced in size or avoided entirely. The location of such edges/steps is indicated generally by reference X in FIG. 1e. The device 10 may therefore smoothly transition at these edges to the outer surface 100 of the bone. The device 10 may be flush with the outer surface 100 of the bone at these edges.

As best seen in FIG. 1a, the connection portion 13 also has a reduced width or waist towards its midline to reduce the size of the connection portion 13.

As discussed above, the orthopaedic device 10 illustrated in FIGS. 1a to 1e takes a neutral (or balanced) configuration. In an alternative embodiment of the present disclosure illustrated in FIGS. 2a to 2d, the device may take an offset (or unbalanced) configuration in which the device has a non-symmetrical shape.

In more detail, FIGS. 2a to 2d show a device 20 that is similar to the device 10 of FIGS. 1a to 1e and is to be fixed to bone in substantially the same manner, but which has an offset, non-symmetrical configuration. This different configuration enables the device 20 to be used with a bone having a different outer surface profile from that illustrated in FIG. 1e, e.g., a profile that is distinctly non-symmetrical either side of the growth plate.

The device 20 includes a first end portion in the form of a first end cup 21, a second end portion in the form of a second end cup 22 and a connection portion 23 connected between the first and second end cups 21, 22. The first and second end cups 21, 22 are substantially identical to the end cups 11, 12 described above with reference to FIGS. 1a to 1e.

The connection portion 23 is a substantially planar element but with a bend 233 that is located nearer to the first end cup 21 than the first end cup 22. The connection portion 23 includes an inner (or bottom) surface 231 on one side and an outer (or top) surface 232 on an opposite side. The first and second end cups 21, 22 protrude in an inward direction relative to the connection portion 23 such that shoulder regions 212, 222 are formed at interfaces between inner surfaces 211, 221 of the first and second end cups 21, 22 and the inner surface 231 of the connection portion 23. In particular, a first shoulder region 212 is formed at the interface between the inner surface 211 of the first end cup 21 and the inner surface 231 of the connection portion 23 at a first end of the connection portion 23, and a second shoulder region 222 is formed between the inner surface 221 of the second end cup 22 and the inner surface 231 of the connection portion 23 at a second end of the connection portion 23.

Unlike the device 10 illustrated in FIGS. 1a to 1e, however, the first and second shoulder regions 212, 222 of the device 20 each define different angles α, β. In particular, the first shoulder region 212 defines an angle β of approximately 90 degrees and the second shoulder region defines an angle α of approximately 130 degrees. Nevertheless, the first and second end cups 21, 22 still protrude along respective first and second axes 216, 226 that are parallel to each other. In the offset configuration, bottom walls 214, 224 of the end cups 21, 22, which include openings 213, 223, extend across different planes 217, 227.

Figure 3:
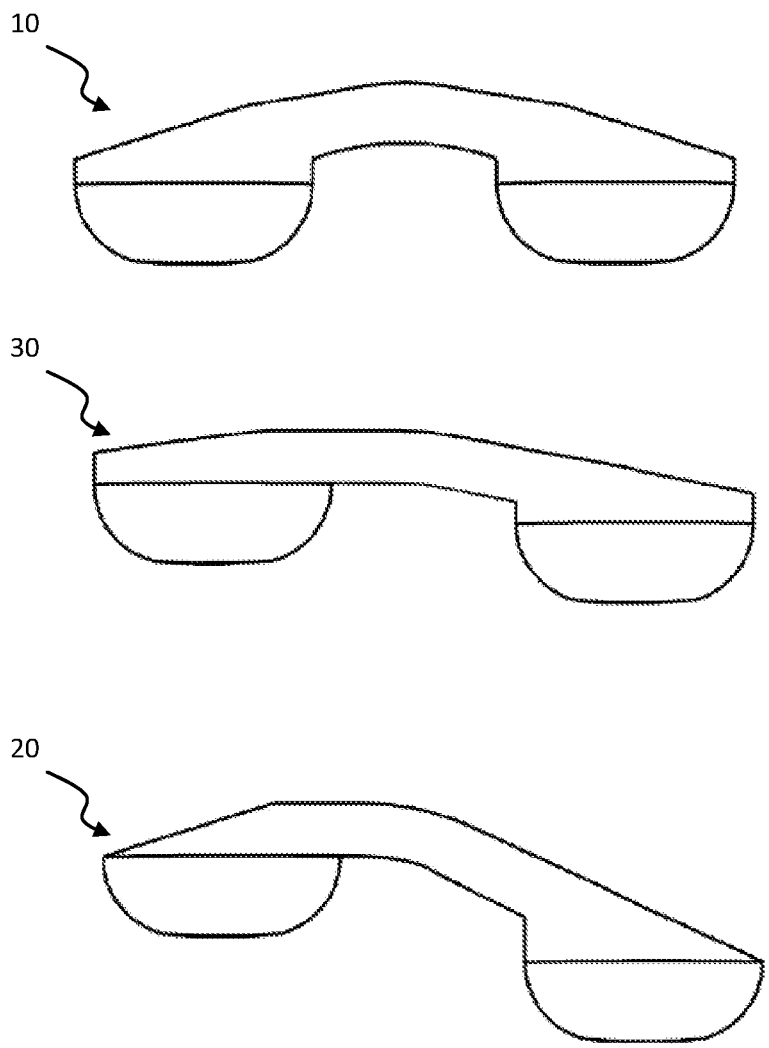
FIG. 3 shows a comparison of lateral views of the orthopaedic devices of FIGS. 1c and 2c along with a further orthopaedic device according to an embodiment of the present disclosure.

The degree of offset of the device 20 may be varied. For example, as shown in FIG. 3, an alternative orthopaedic device 30 may be provided that is offset, but not to the same extent as the fixation device 20 described above with reference to FIGS. 2a to 2e.

Moreover, the sizing of the orthopaedic devices may be varied, including the lengths of the connection portions, the sizes of the end cups and/or openings in the end cups (e.g., to enable receipt of bone screws with different diameters) and other features. In some embodiments, the end portions can be replaced with plate-like elements, where the heads of bone screws are not contained within the end portions, and protrude therefrom.

A method of implanting the orthopaedic device 20 of FIGS. 2a to 2d is now described with reference to FIGS. 4a to 4j. The same or a similar method may be used to implant orthopaedic devices according to other embodiments disclosed herein.

Figure 4A:
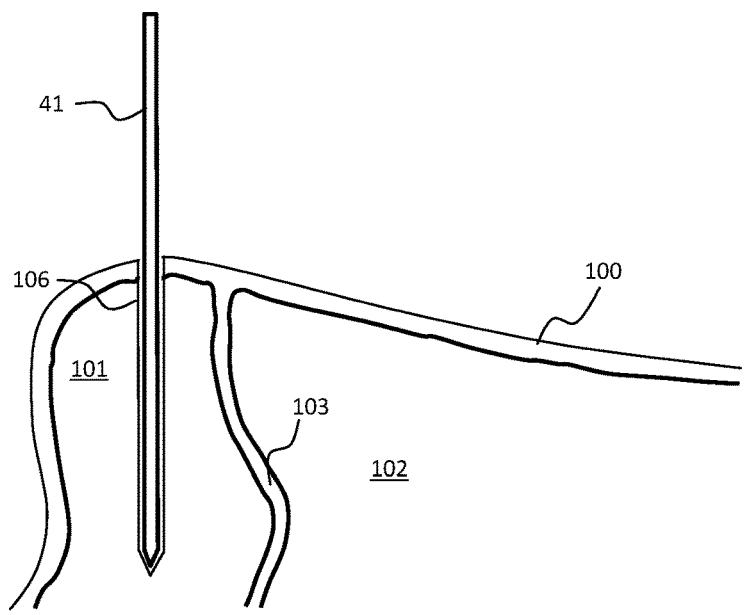
FIGS. 4a to 4j illustrate a method of implanting an orthopaedic device according to an embodiment of the present disclosure in a bone.

With reference to FIG. 4a, a first guide member 41 is used to form a first elongated bore 106 in the first bone region 101.

Figure 4B:
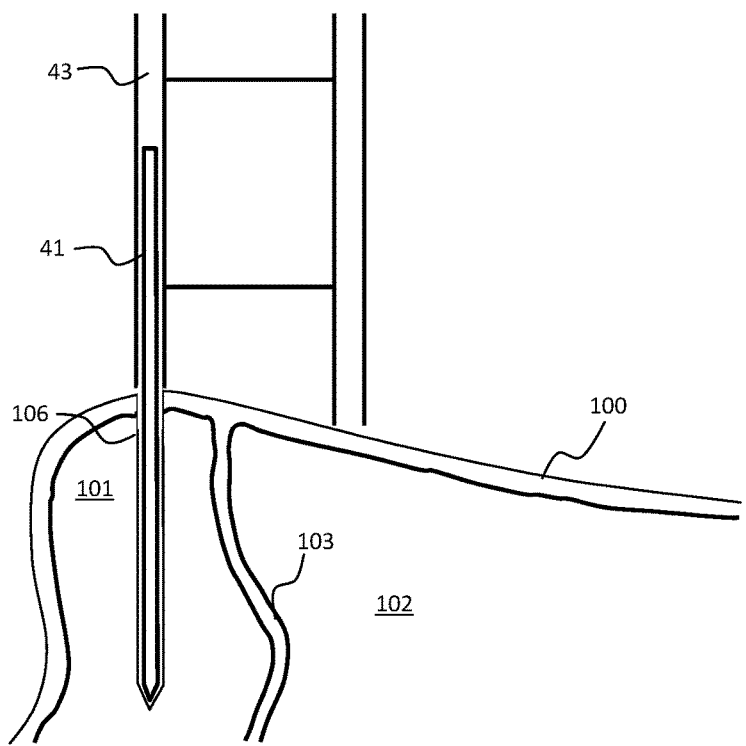

With reference to FIG. 4b, a spacer 43 is mounted to the first guide member 41.

Figure 4C:
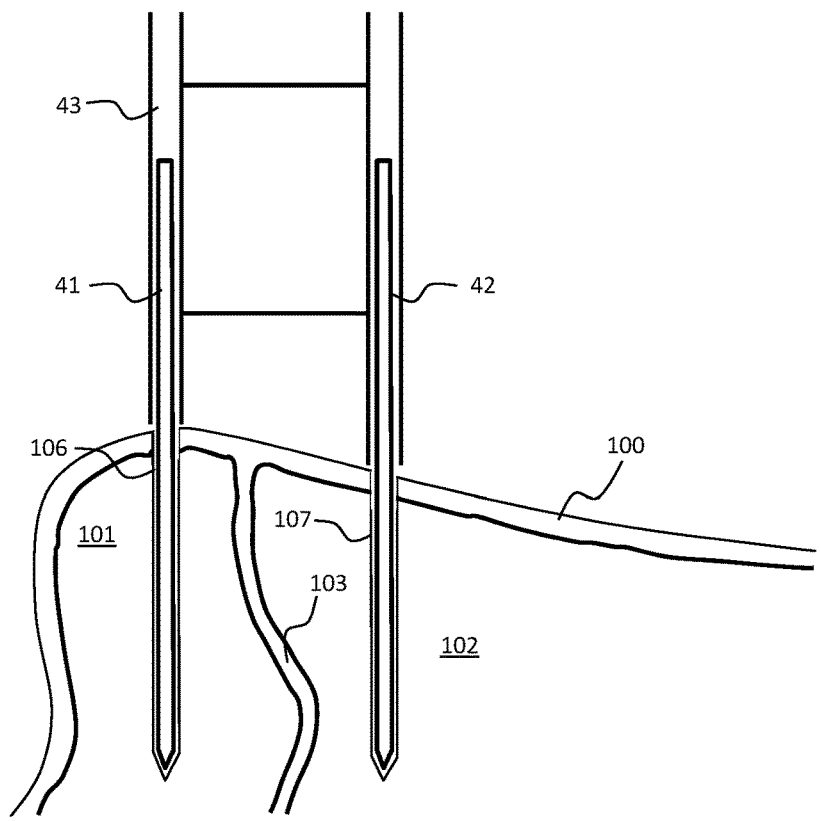

With reference to FIG. 4c, the spacer 43 acts as a guide to position a second guide member 42 to form a second elongated bore 107 in the second bone region 102. The second elongated bore 107 is parallel to the first elongated bore 106 and is separated from the first elongated bore 106 by a distance corresponding substantially to the distance between the first and second axes 216, 226 of the orthopaedic device 20.

Figure 4D:
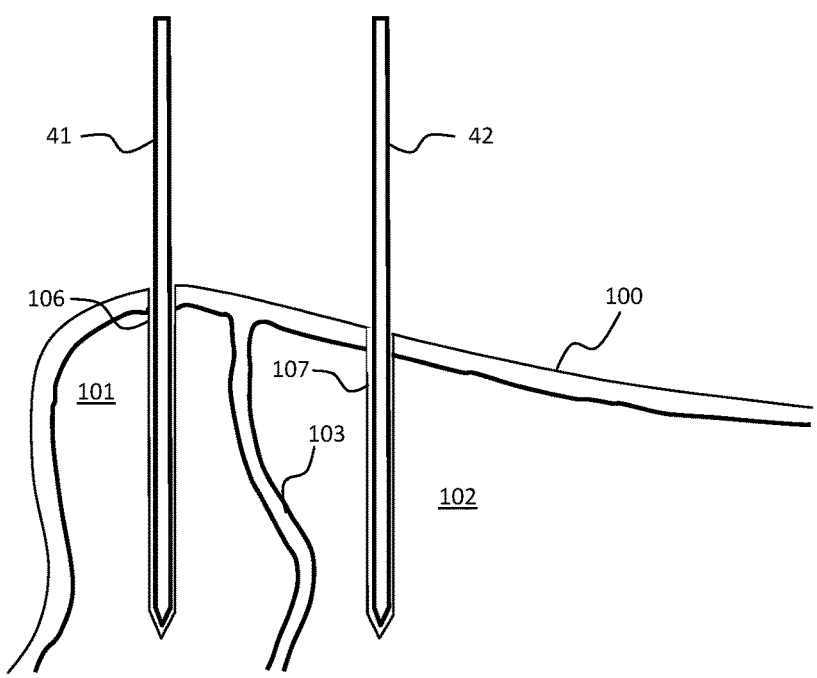

With reference to FIG. 4d, the spacer 42 is removed leaving the first and second guide members 41, 42 in position at the bone.

Figure 4E:
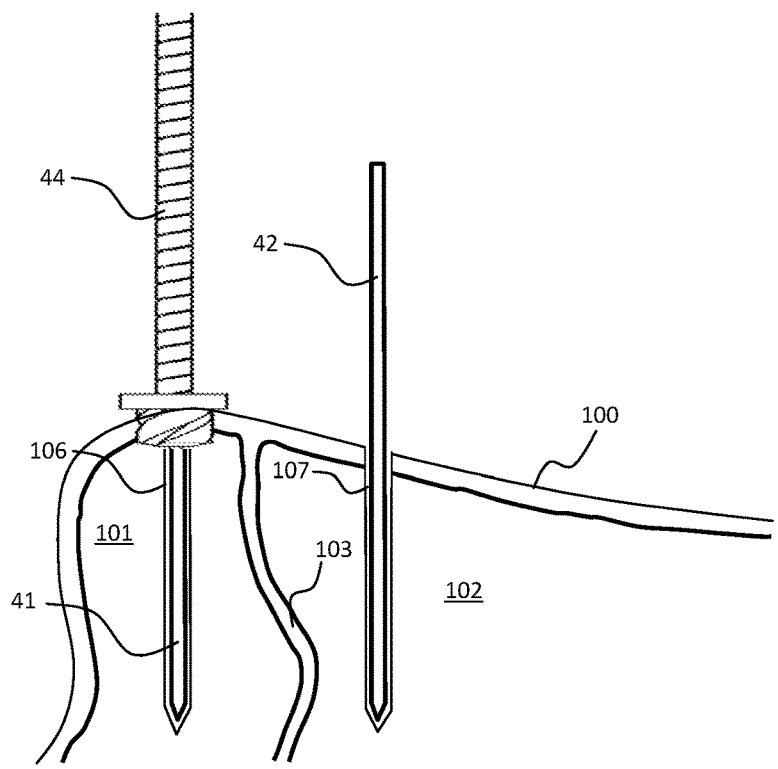

With reference to FIG. 4e, a counterbore drill bit 44 having central lumen is provided, the central lumen being passed over the first guide member 41 so that the drill bit 44 can contact, and form a first recess 104 at, the outer surface 100 of the first bone region 101. The first recess 104 is formed at the end of the first elongated bore 106 and has a larger diameter than the first elongated bore 106.

Figure 4F:
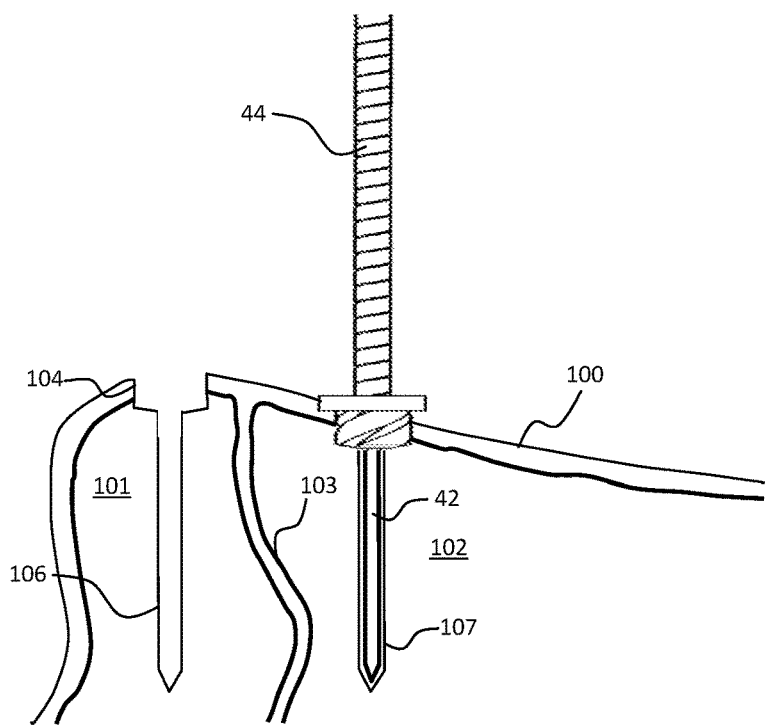

With reference to FIG. 4f, the counterbore drill bit 44 is then passed over the second guide member 42 to contact, and form a second recess 105 at, the outer surface 100 of second first bone region 102. The second recess 105 is positioned at the end of the second elongated bore 107 and has a larger diameter than the second elongated bore 107. The guide members 41, 42 and drill bit 44 are removed.

Figure 4G:
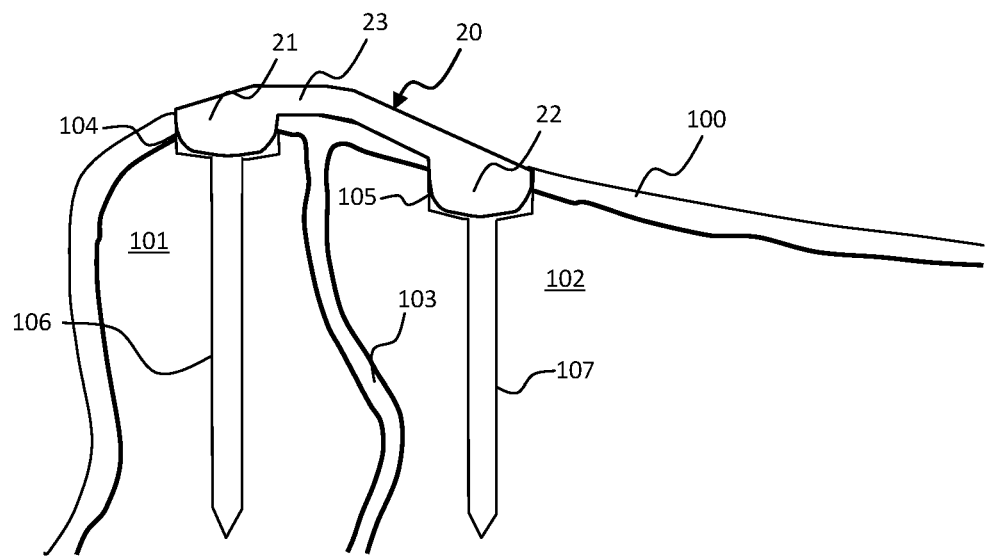

With reference to FIG. 4g, the orthopaedic device 20 is brought into position at the outer surface 100 of the bone such that the connection portion 23 of the device 20 extends across the outer surface 100 of the bone and the first and second end cups 21, 22 protrude into the first and second recesses 104, 105, respectively.

Figure 4H:
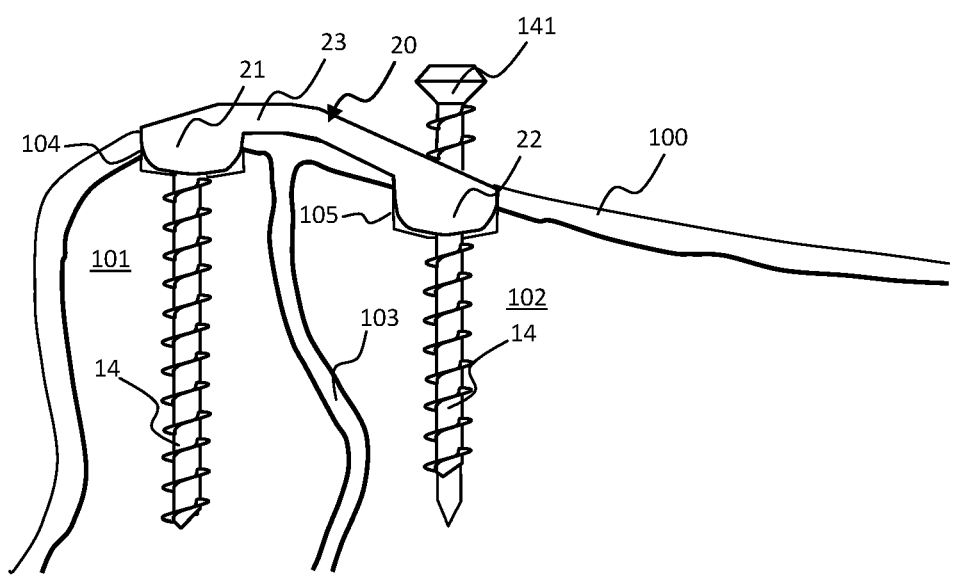

With reference to FIG. 4h, bone screws 14 are used to fix the first and second end cups 21, 22 to the first and second bone regions 101, 102 by travelling through the openings in the end cups 21, 22 and along the first and second elongated bores 106, 107 into the bone. The first and second elongated bores 106, 107 act as pilot holes for the bone screws 14.

In this embodiment, the bone screws 14 used to fix the first and second end cups 21, 22 in position are solid screws. In alternative embodiments, one or more of the bone screws may be cannulated (e.g., they may contain a central bore) so they may be extended over the guide members 41, 42 in order to be inserted into openings in the end cups 21, 22. Thus, rather than remove the guide members 41, 42 before insertion of the bone screws (and the device 20), the guide members 41, 42 may be kept in place until the device 20 and cannulated bone screws are inserted. To advance the cannulated bone screws, a cannulated screwdriver may be used.

Cross-sectional views of apparatus of the present disclosure are generally provided in FIGS. 1e and 4e to 4h discussed above. However, for ease of illustration, the orthopaedic device 20, counterbore drill bit 44 and bone screws 14 are not represented in cross-section in these Figures. On the other hand, FIG. 4i does show the orthopaedic device 20 in cross-section. As can be seen, the heads 141 of the bone screws 14 are fully located within the end cups 21, 22 and abut the outer surface of the bottom walls 214, 224 of the cups 21, 22. Meanwhile, the threaded shafts 142 extend through the openings 213, 223 in the cups 21, 22 and into the bone.

Figure 4I:
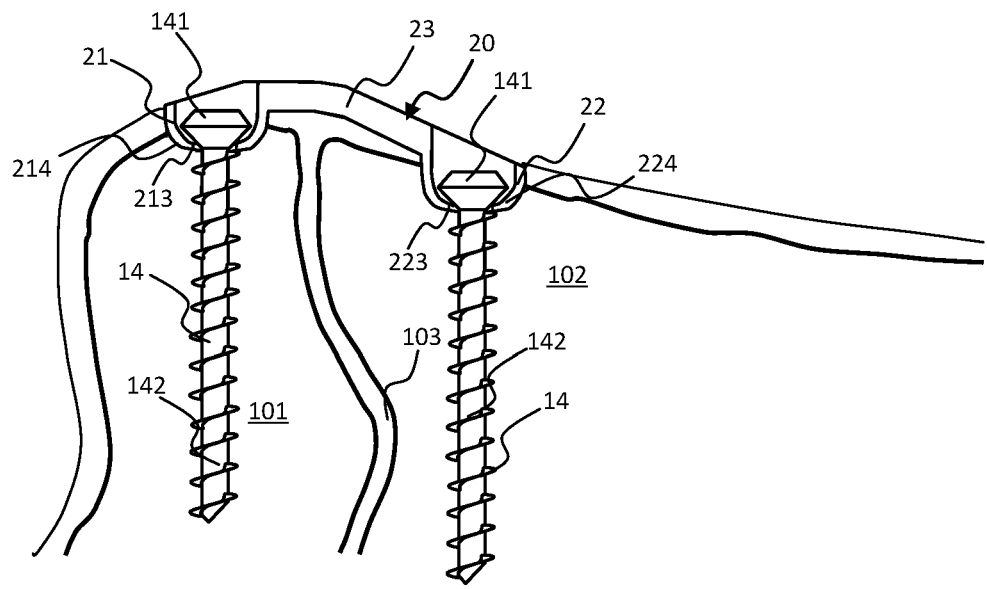
Figure 4J:
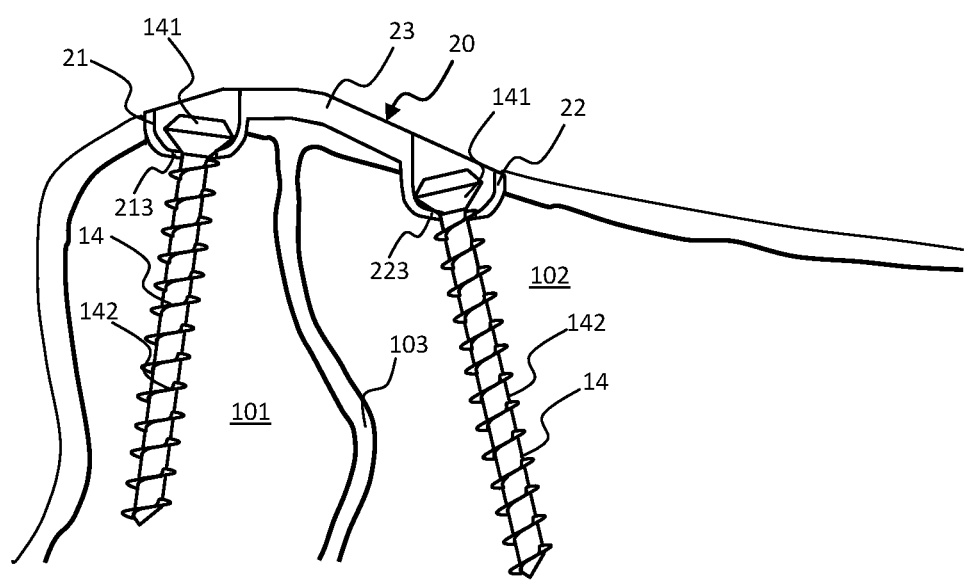
Figure 5A:
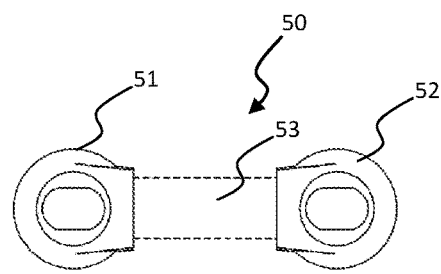
FIGS. 5a to 5d show a top plan view, top oblique view, lateral view, and bottom oblique view, respectively, of an orthopaedic device according to another embodiment of the present disclosure
Figure 5B:
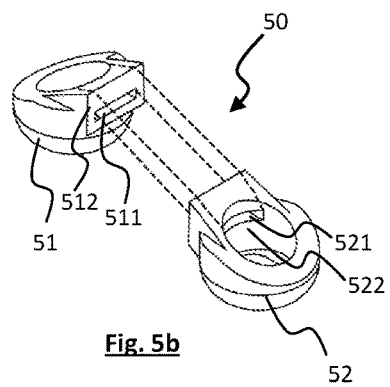
Figure 5C:
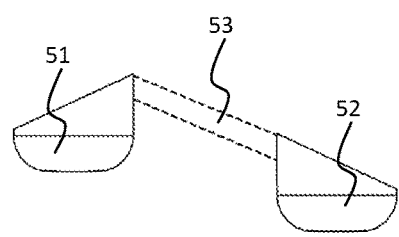
Figure 5D:
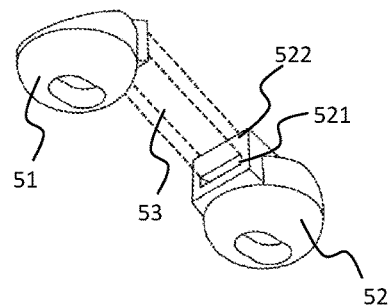

As represented in FIG. 4i, the bone screws 141 extend parallel to each other, along first and second axes of the cups 21, 22. This provides a suitable orientation for the bone screws 14 upon implantation of the orthopaedic device 20, although other orientations are possible. Following implantation, bone growth can cause the bone screws 14 to rotate (pivot) relative to each other as illustrated in FIG. 4j. So that rotation of the bone screws can be accommodated by the orthopaedic device 20, the end cups 21, 22 have size and shape that permit rotation of the heads 141 of the bone screws 14 within the cups 21, 22. Moreover, the openings 213, 223 in the cups 21, 22 are elongated to accommodate rotation of the shafts 142 of the bone screws 14.

The orthopaedic devices according to embodiments of the present disclosure described above with reference to FIGS. 1a to 3 are each formed in one-piece from surgical grade metal, e.g., cobalt chromium alloy, titanium or stainless steel. Nevertheless, the orthopaedic devices may be formed in more than one piece and/or from different materials. For example, the end portions may be formed of different material from the connection portion. The end portions may be rigid and the connection portion may be non-rigid, for example.

An orthopaedic device 50 according to an embodiment of the present disclosure and which is formed of multiple pieces is illustrated in FIGS. 5a to 5d. The orthopaedic device 50 is similar to the devices 10, 20, 30 of FIGS. 1a to 3, and is to be fixed to bone in substantially the same manner. However, the device 50 has a connection portion 53 that comprises a flexible link, in particular an elongate flexible tape, which tape extends between rigid end cups 51, 52 formed of surgical grade metal. While the tape is flexible and easily compressible, the tape is strong under tension. Accordingly, the device 50 can maintain resistance against bone growth in a similar manner to the devices 10, 20, 30 of FIGS. 1a to 3. However, the flexible nature of the tape, and the manner in which the tape joins to rigid end cups 51, 52, enables the device 50 to adjust between a neutral configuration, e.g., similar to the device 10 described above with reference to FIGS. 1a to 1e, and offset configurations, e.g., similar to the devices 20, 30 described above with reference to FIGS. 2a to 3. The device 50 is therefore adaptable for use with bones having a wide variety of surface profiles. Moreover, the connection portion 53 of the device 50 can be formed of a tape material that permits ingrowth of bone. The flexible material can be formed of a woven mesh or otherwise, for example.

The tape of the connection portion 53 of the device 50 is illustrated in FIGS. 5a to 5d using dotted lines so that visibility of the end cups 51, 52 is not obscured. The end cups 51, 52 can be configured similarly to end cups described with respect to previous embodiments, except for the nature of their join with the connection portion 53. Each end cup 51, 52 includes a slot 511, 512 in an opposing side wall 512, 522 of the cup 51, 52 to achieve the join. The flexible tape of the connection portion 53 extends through each slot and forms a loop between the two cups 51, 52. Nevertheless, alternative end portions or end cups may be employed in orthopaedic devices according to embodiments of the present disclosure that utilise a connection portion formed of a flexible link such as elongated flexible tape. The end portions may or may not be configured for receipt in recesses in bone, for example.

Figure 6A:
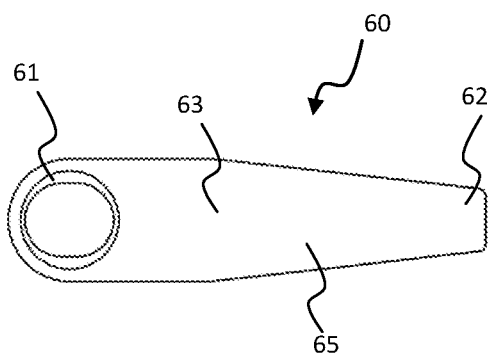
FIGS. 6a and 6b show a top plan view and a lateral view, respectively, of an orthopaedic device according to another embodiment of the present disclosure.
Figure 6B:
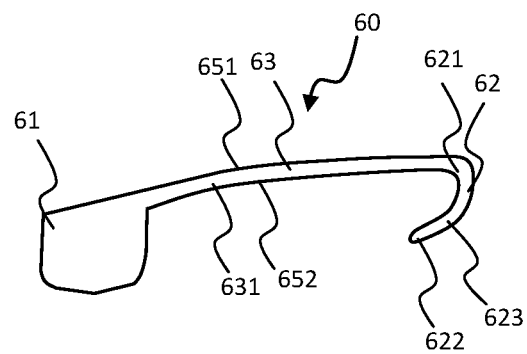
Figure 6C:
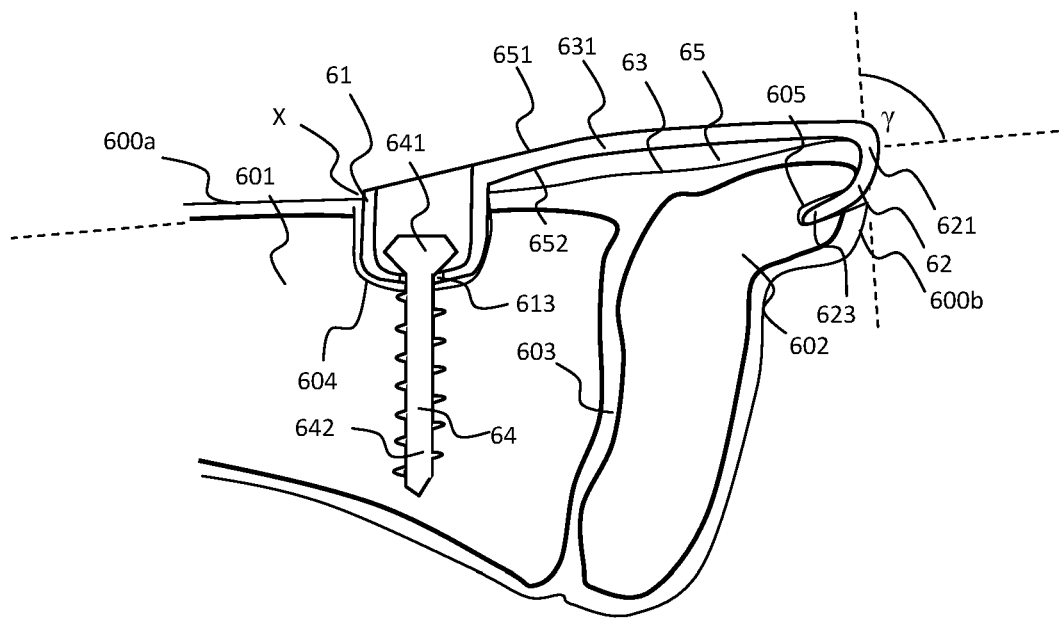
FIG. 6c shows a cross-sectional view of the device of FIGS. 6a and 6b implanted at a bone.

An orthopaedic device 60 according to another embodiment of the present disclosure is illustrated in FIGS. 6a and 6b. A cross-sectional view of the device 60 implanted at a bone is illustrated in FIG. 6c. In accordance with devices of preceding embodiments, the device 60 can fix together first and second regions of bone 601, 602 separated by a growth plate 603. The device 60 includes a first end portion 61, a second end portion 62 and a connection portion 63 connected between the first and second end portions 61, 62. The first end portion 61 is adapted to be fixed to the first bone region 601 and the second end portion 62 is adapted to be fixed to the second bone region 602, whereupon the connection portion 603 extends cross the outer surface of the bone including an outer surface of the growth plate 603. As for embodiments discussed above, the first end portion 61 is in the form of a first end cup 61. However, in this embodiment, the second end portion 62 is in the form of a hook 62 rather than a second end cup.

The hook 62 is formed by a bend in an elongate plate 65 that is connected to the first end cup 61, which plate also forms the connection portion 63. The plate 65 has substantially planar top and bottom surfaces 651, 652. However, a bend 621 is provided in the plate 65, adjacent an opposite end of the plate 65 from the first end cup 61, such as to form the hook 62. The bend 621 that forms the hook 62 turns through an angle of about 170 or 180 degrees in this embodiment, although other angles, such as angles of at least 90 degrees, at least 120 degrees, or at least 150 degrees, are possible. A further minor bend 631 in the plate 65 is provided at the connection portion 63, to enable the connection portion 63 to avoid obstruction with the outer surface of the bone.

The top and bottom surfaces 651, 652 of the plate 65 each taper in width towards a distal end 622 of the hook 62. The hook 62 therefore becomes narrower in width towards its distal end 622, while its thickness remains substantially the same. The narrowing of the hook 62 makes it possible for a distal end portion 623 of the hook 62 to be received into a relatively small second recess 605 in the second bone region 602.

The purpose of the orthopaedic device 60 of the present embodiment is substantially the same as the orthopaedic devices 10, 20, 30, 50 of preceding embodiments. In this regard, when the first and second end portions 61, 62 are fixed to the first and second bone regions 601, 602, the device 60 prevents or limits growth of the growth plate 603 at a region therebetween. Moreover, the first end cup 61 has a similar configuration to the end cups of preceding embodiments. In this regard, the first end cup 61 is adapted to be located in a first recess 604 at the first bone region 601. Further, a head 641 of a first bone screw 64 is adapted to be received in the first end cup 61 while a threaded shaft 642 of the first bone screw 64 extends through an opening 613 in the first end cup 61 and into the first bone region 601. Again, the head 641 of the first bone screw 64 is entirely locatable within the first end cup 61 such that the head 641 does not protrude from the orthopaedic device 60.

As seen in FIG. 6c, when deployed, the hook 62 extends around an end of the second bone region 602 whereupon the distal end portion 623 of the hook 62 locates in a second recess 605 formed in the second bone region 602. Meanwhile, the first end cup 61 locates in the first recess 604 in the first bone region 601.

The first end cup 61 enters the first recess 604 via an opening in a first outer bone surface 600a of the first bone region 601, and the hook 62 enters the second recess 605 via an opening in a second outer bone surface 600b of the second bone region 602. The first outer bone surface 600a is a lateral surface of the bone whereas the second outer bone surface 600b is a distal or proximal end surface of the bone. The first and second surfaces 600a, 600b extend at an angle α relative to each other of about 90 degrees in this embodiment, although other angles are possible depending on the contours of the surfaces and the positioning of the recesses. Since the bend 621 forming the hook 62 has an angle of about 180 degrees, the hook braces against the second surface 600b in direct opposition to the direction of growth of the bone.

As illustrated in FIG. 6c, the first bone region 601 is specifically the metaphysis of a long bone and the second bone region 602 is specifically the epiphysis of the long bone. The hook may be used in conjunction with the epiphysis because there may be insufficient space at the epiphysis for the second bone region to receive a second end cup and/or a second bone fixation device. The hook may provide a less invasive means of fixation to the epiphysis.

In the present embodiment, the orthopaedic device 60 is again formed in one-piece from surgical grade metal, e.g., cobalt chromium alloy or titanium. However, alternative materials may be used.

Figure 7A:
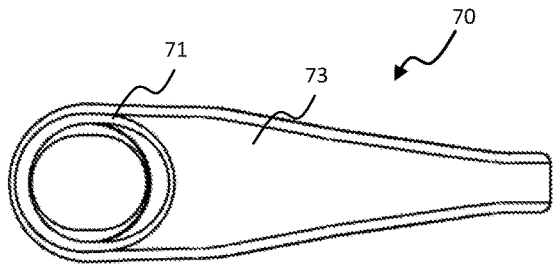
FIGS. 7a to 7c show a top plan view, lateral view and top oblique view, respectively, of an orthopaedic device according to another embodiment of the present disclosure.
Figure 7B:
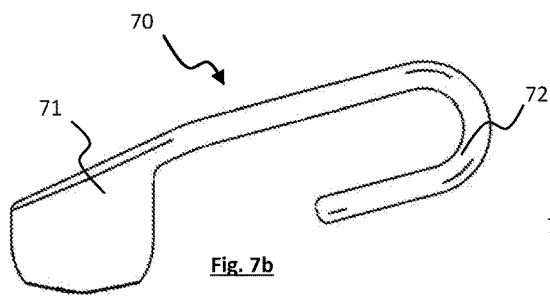
Figure 7C:
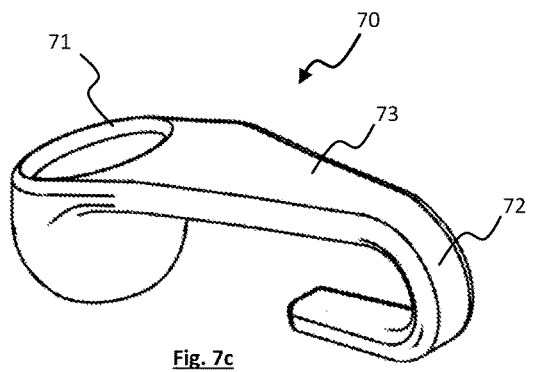

An orthopaedic device 70 that is a variation of the orthopaedic device 60, discussed above with reference to FIGS. 6a to 6c, is illustrated in FIGS. 7a to 7c. The orthopaedic device 70 has similar features to the device 60, including a first end cup 71, a hook 72 and a connection portion 73 extending therebetween. However, the profile of the device 70 is generally more robust to avoid undesirable unbending of the hook 72 during use. Moreover, the connection portion 73 extends at a relatively steep angle from the first end cup 71. Further, the width of the connection portion 73 tapers towards the hook 72, but the width of the hook 72 remains substantially constant along its length.

Figure 8:
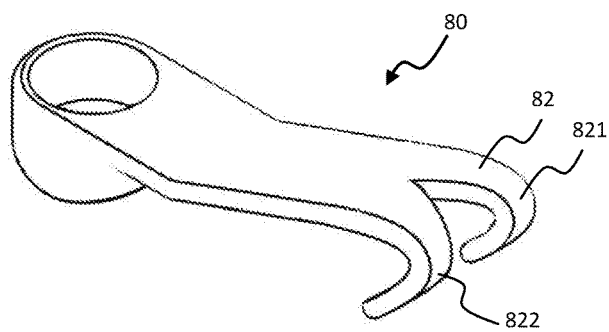
FIG. 8 shows a top oblique view of an orthopaedic device according to another embodiment of the present disclosure.

Another variation of the orthopaedic device 60 discussed above with reference to FIGS. 6a to 6c, is illustrated in FIG. 8. In FIG. 8, an orthopaedic device 80 is illustrated that has a similar configuration to the device 60 except most notably for the provision of a hook 82 that comprises two prongs 821, 822, the two prongs 821, 822 being for receipt in respective second recesses at the second bone region. Multiple second recesses may therefore be provided, of relatively smaller size, while achieving a similar or even enhanced degree of engagement between the orthopaedic device 80 and the second bone region.

According to an embodiment of the present disclosure, a method of implanting an orthopaedic device including a first end cup and a hook, e.g., in accordance with the orthopaedic devices 60, 70, 80 of FIGS. 6a to 8, is now described. The method is illustrated using the orthopaedic device 60 of FIGS. 6a to 6c. The orthopaedic device 60 is implanted in bone comprising first and second bone regions 601, 602 to prevent or limit growth of a growth plate 603 at a region between the first and second bone regions 601, 602.

Figure 9A:
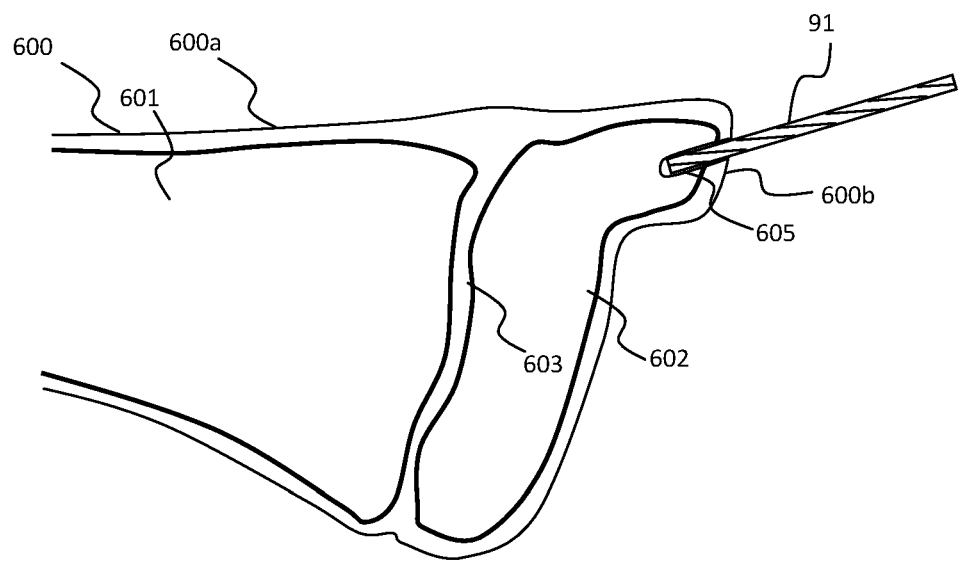
FIGS. 9a to 9i illustrate a method of implanting an orthopaedic device according to another embodiment of the present disclosure at a bone.

With reference to FIG. 9a, a drill 91 or other type of boring tool is used to form a second recess 605 in the second bone region 602, the second recess opening at a second outer bone surface 600b of the second bone region 602.

Figure 9B:
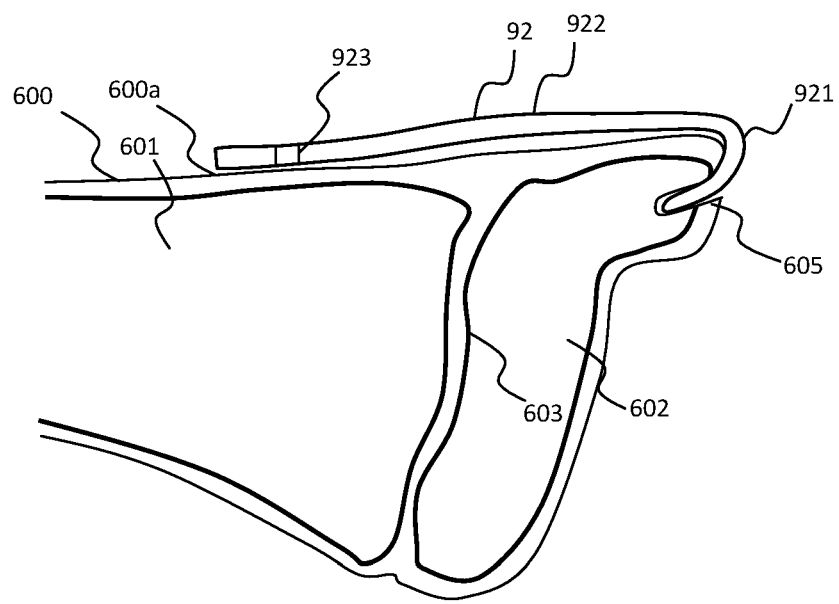

With reference to FIG. 9b, a jig 92, which has a shape and configuration that is similar to the orthopaedic device 70, except for the omission of a first end cup, is introduced. Specifically, a distal end portion of a hook 921 of the jig 92 is located in the second recess 605 of the second bone region 602, whereupon a connection portion 922 of the jig 921 extends from the hook, across the outer surface 600 of the bone, whereupon a guide opening 923 of the jig 92 is positioned adjacent a first outer bone surface 600a of the first bone region 601.

Figure 9C:
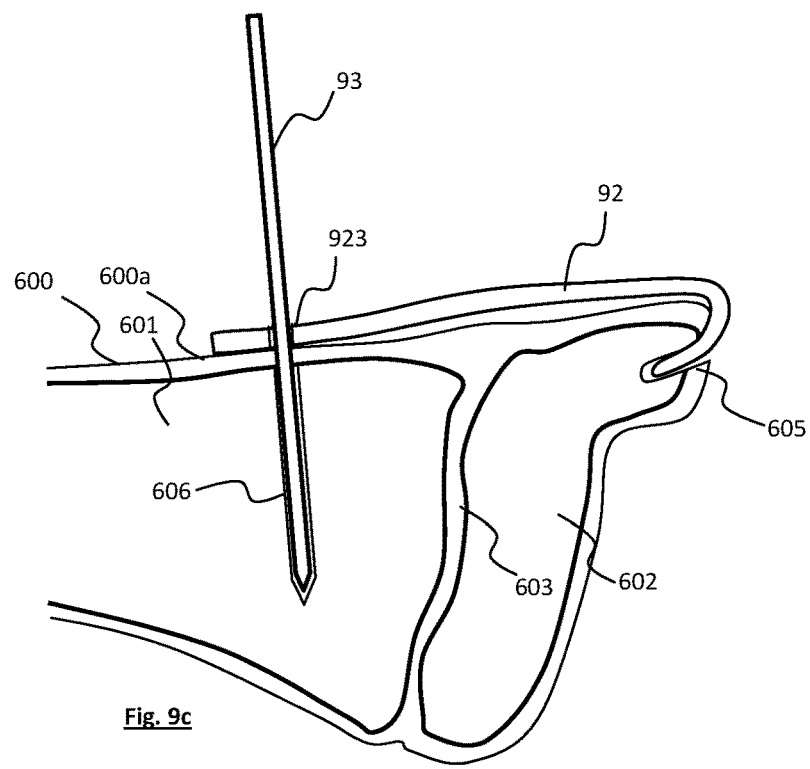

With reference to FIG. 9c, the guide opening 923 in the jig 92 acts as a guide to position a guide member 93 in the first bone region 601. The guide member 93 is used to form an elongated bore 606 in the first bone region 601.

Figure 9D:
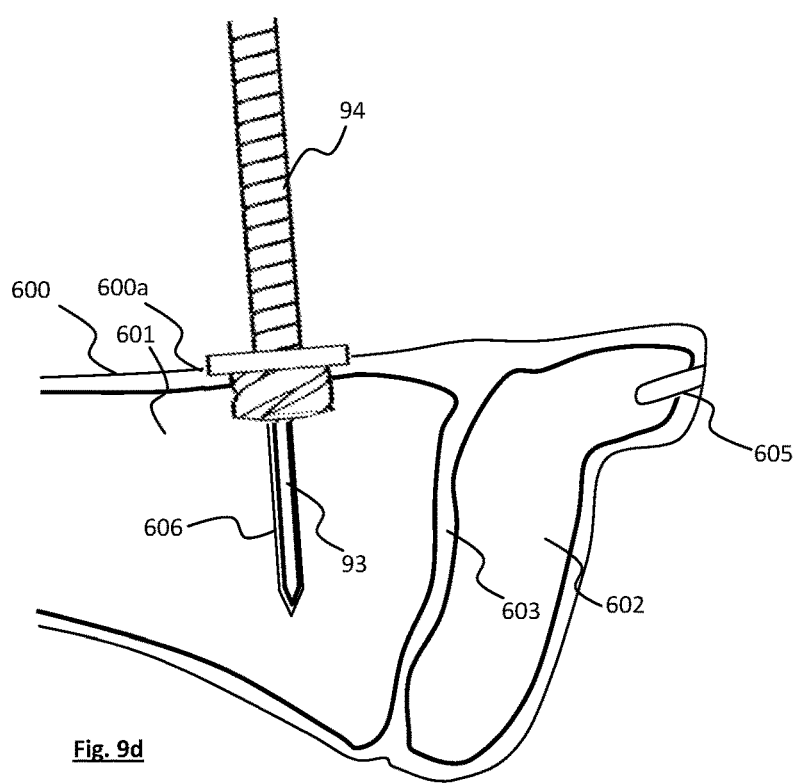

With reference to FIG. 9d, the jig 92 is removed leaving the guide member 93 in position in the elongate bore 606. A counterbore drill bit 94 having central lumen is then provided, the central lumen being passed over the guide member 93 so that the drill bit 94 can contact, and form a first recess 604 at, the outer surface 600 of the first bone region 601.

Figure 9E:
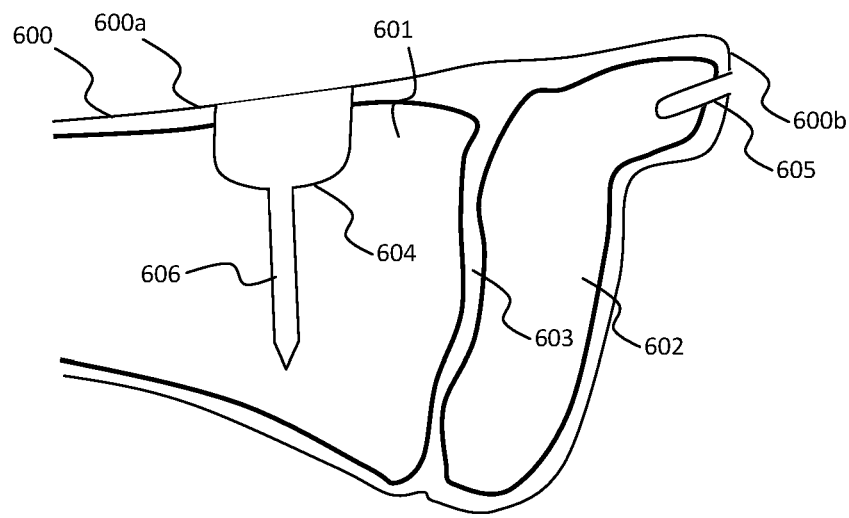

With reference to FIG. 9e, the counterbore drill bit 94 is then removed. As can be seen, the first recess 604 opens at the first outer bone surface 600a of the first bone region 601 and the first recess 604 is formed at the end of the elongated bore 606. The first recess 604 has a larger diameter than the elongated bore 606.

Figure 9F:
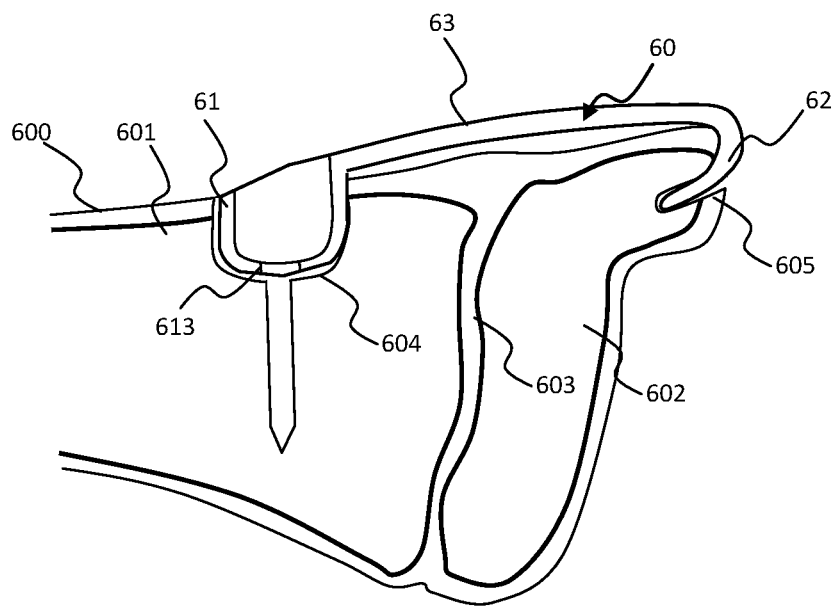

With reference to FIG. 9f, the orthopaedic device 60 is brought into position at the outer surface 600 of the bone such that the first end cup 61 protrudes into the first recesses 604, the hook 62 protrudes into the second recess 605 and the connection portion 63 extends across the outer surface 600 of the bone.

Figure 9G:
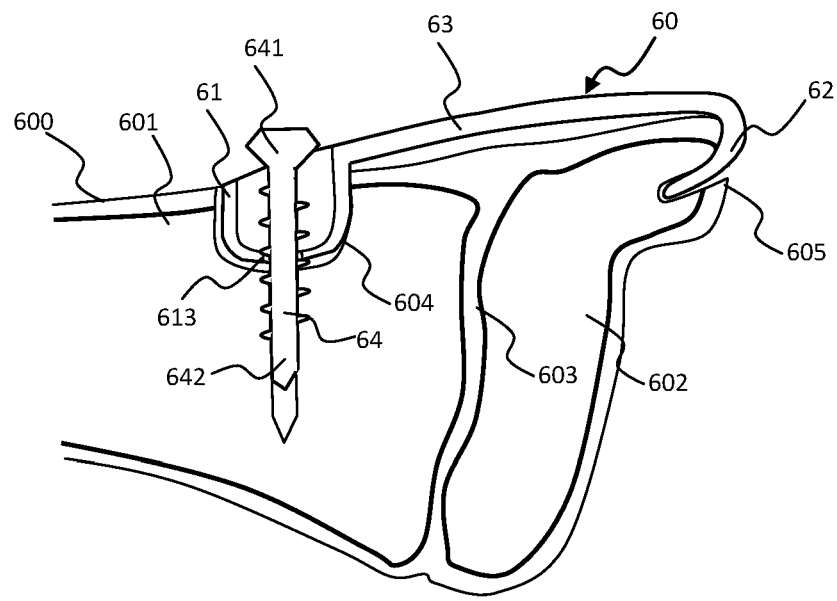
Figure 9H:
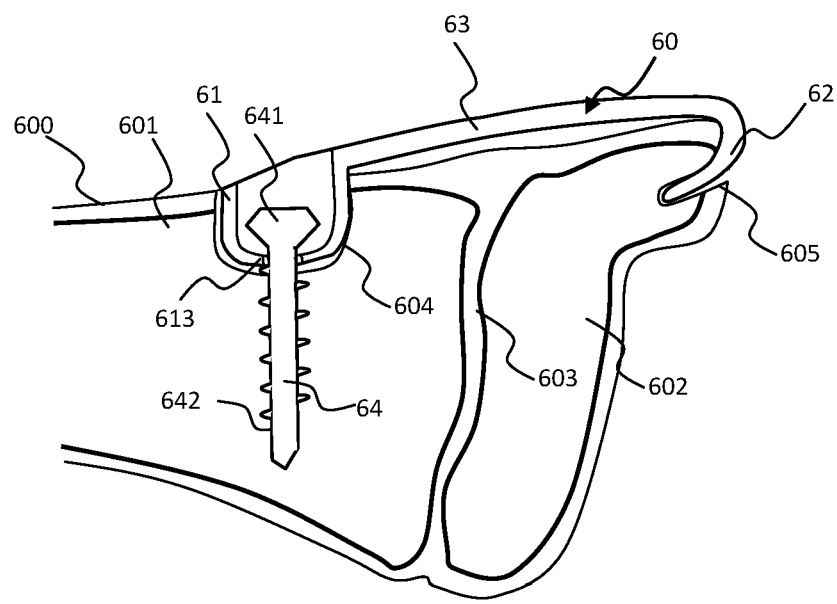

With reference to FIGS. 9g and 9h, a bone screw 64 is used to fix the first end cup 61 to the first bone region 601 by travelling through an opening 613 in the first end cup 61 along the elongated bore 606 and into the bone. The elongated bore 606 acts as a pilot hole for the bone screw 64. The fixing of the first end cup 61 to the bone using the bone screw 64 also causes fixing of the hook 62. In effect, once the bone screw 64 is in place, the hook 62 cannot be removed from the second recess 605.

In this embodiment, the bone screw 64 used to fix the first end cup 61 in position is a solid screw. In alternative embodiments, a cannulated bone screw may be used that extends over the guide member 93.

Figure 9I:
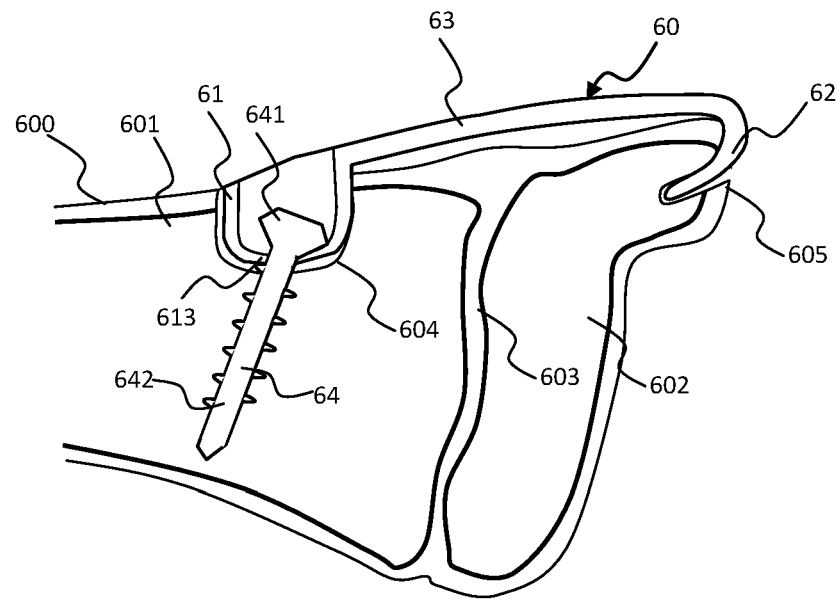

As represented in FIG. 9i, following implantation, bone growth can cause the bone screw 64 to rotate (pivot) relative to the first end cup 61. So that rotation of the bone screw can be accommodated by the orthopaedic device 60, the end cup 61 has a size and shape that permits rotation of the head 641 of the bone screw 64 within the cup 61. Moreover, the opening 613 in the cup 61 is elongated to accommodate rotation of the shaft 642 of the bone screw 64.

Figure 10:
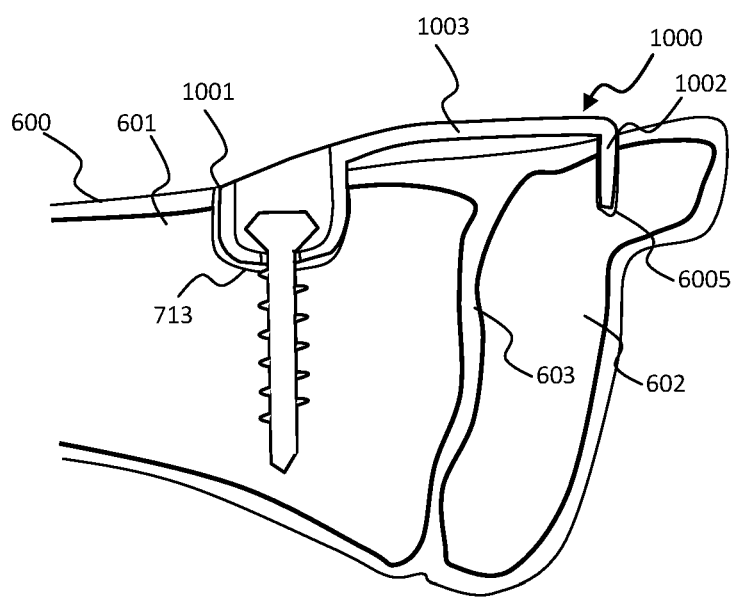
FIG. 10 shows a cross-sectional view of an orthopaedic device according to yet another embodiment of the present disclosure implanted at a bone.

Another variation of the orthopaedic device 60 discussed above with reference to FIGS. 6a to 6c, is illustrated in FIG. 10. In FIG. 10, an orthopaedic device 1000 is illustrated that has substantially the same configuration as the device 60 except for the configuration of the connection portion 1003 and second end portion. In the embodiment of FIG. 10, the connection portion 1003 is shorter, and the second end portion comprises a blade 1002, rather than a hook. The blade extends relative to the connection portion 1003 at an angle of about 100 degrees only. The design is such that the blade 1002 can protrude into a second recess 6005 that is open to a lateral surface of the bone, rather than an end surface of the bone.

Figure 11A:
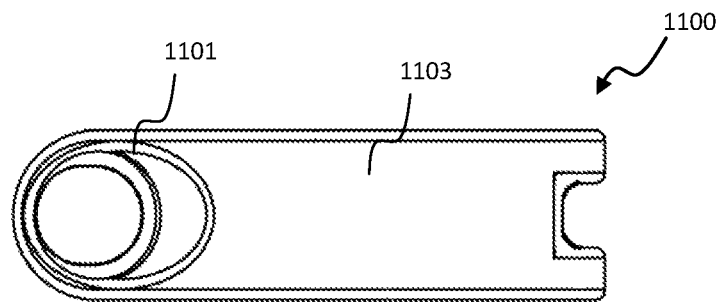
FIGS. 11a to 11c show a top plan view, top oblique view and lateral view, respectively, of an orthopaedic device according to yet another embodiment of the present disclosure.
Figure 11B:
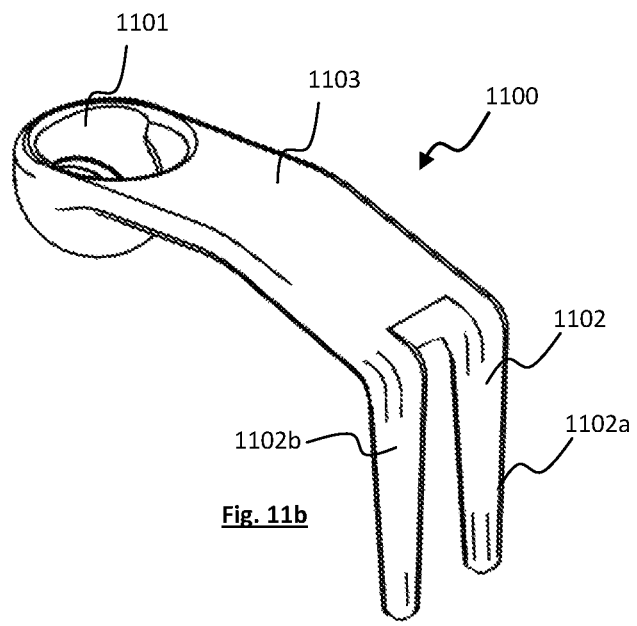
Figure 11C:
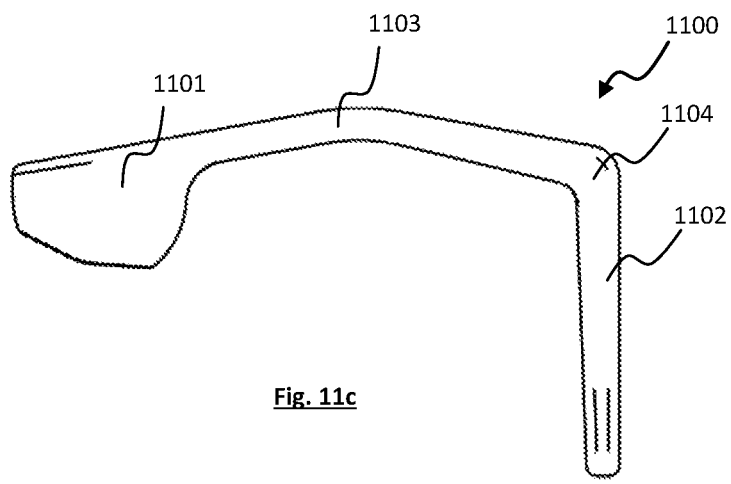

An orthopaedic device 1100 providing yet another variation of the orthopaedic device 60 discussed above with reference to FIGS. 6a to 6c, is illustrated in FIGS. 11a to 11c. The orthopaedic device 1100 is similar to the orthopaedic device 1000 of FIG. 10. However, rather than a blade, the second end portion of the orthopaedic device 1100 comprises a staple 1102. The staple 1102 comprise two spaced apart prongs 1102a, 1102b that extend substantially parallel to each other and that each extend at an angle relative to the connection portion of about 100 degrees. Each prong 1102a, 1102b is substantially straight but tapers in its thickness towards its distal end. Each prong 1102a, 1102b is adapted to project into respective second recesses formed in the second bone region. A connection portion 1103 of the device 1000 that extends between the staple 1102 and a first end cup 1101 thickens towards the staple 1102. Accordingly, a corner region 1104 between the connection portion 1103 and the staple 1102 is relatively thick, reducing the likelihood that the staple might bend relative to the connection portion 1103 during use.

The orthopaedic devices according to embodiments of the present disclosure described above with reference to FIGS. 6a to 11c are each formed in one-piece from surgical grade metal, e.g., cobalt chromium alloy, titanium or stainless steel. Nevertheless, the orthopaedic devices may be formed in more than one piece and/or from different materials. For example, the end portions may be formed of different material from the connection portion. The end portions may be rigid and the connection portion may be non-rigid, for example.

In embodiments described above, and as illustrated in FIGS. 4j and 9i, following attachment of the orthopaedic devices to bone using one or more bone screws, the bone screws can undergo a pivotal rotation relative to the orthopaedic devices to accommodate bone growth, particularly at bone regions spaced from the orthopaedic device into which regions the shafts of the bone screws extend. In the embodiment illustrated in FIG. 4j, for example, two bone screws 14, one at each end of the orthopaedic device 20, can rotate in this manner upon growth. To enable this, the end cups 21, 22 of the orthopaedic device 20 have a size and shape that permits rotation of the heads 141 of the bone screws 14 within the cups 21, 22. Moreover, the openings 213, 223 in the cups 21, 22 are elongated to accommodate rotation of the shafts 142 of the bone screws 14.

In alternative embodiments, however, it can be desirable to restrict pivotal rotation of at least one of the bone screws. It has been found, for example, that pivotal rotation of a bone screw fixed to the epiphysis can in some circumstances cause shifting of the orthopaedic device relative to the surface of the bone to a position where it may interfere with and potentially cause damage to the growth plate.

Figure 12A:
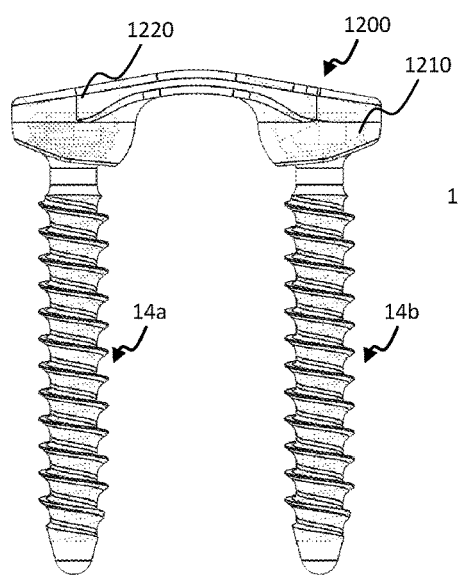
FIGS. 12a and 12b show lateral and cross-sectional lateral views, respectively, of an orthopaedic device according to another embodiment of the present disclosure.
Figure 12B:
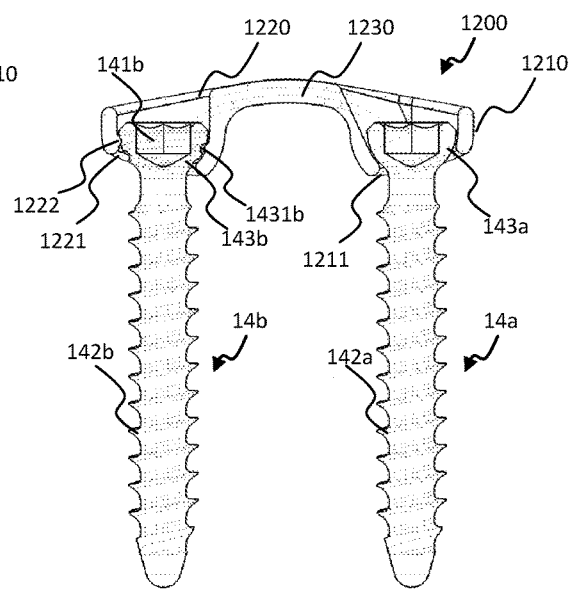

An orthopaedic device 1200 according to an embodiment of the present disclosure, which orthopaedic device 1200 provides an example of how rotation of one of the bone screws can be restricted, is illustrated in FIGS. 12a and 12b. The orthopaedic device 1200 includes a first end portion in the form of a first end cup 1210, a second end portion in the form of a second end cup 1220 and a connection portion 1230 connected between the first and second end cups 1210, 1220. Each of the first and second end cups 1210, 1220 includes a bottom wall having an opening 1211, 1221 to receive a bone screw 14a, 14b. In this regard, the orthopaedic device 1200 is similar to the orthopaedic devices 10, 20, 30 described above with reference to FIGS. 1a to 3, for example. Moreover, in accordance with those orthopaedic devices 10, 20, 30, the second end cup 1220 has a size and shape that permits rotation of the head 143a of a first bone screw 14a within the cup 1210, and the opening 1211 in its bottom wall is shaped to accommodate rotation of the shaft 142a of the bone screw 14a upon bone growth.

The second end cup 1220 differs from the first end cup 1210, however, by virtue of a locking thread 1222 being disposed about the opening 1221 in its bottom wall. The thread 1222 is adapted to threadedly engage with a complimentary thread 1431b disposed on the head 143b of a second bone screw 14b that is to be received in the second end cup 1220. Threaded engagement between the head 143b of the first bone screw 14b and the second end cup 1220 can take place at the same time as the second bone screw 14b is screwed into a second region 1242 of bone.

The threaded engagement between the head 143b of the second bone screw 14b and the second end cup 1220 substantially locks the position of the second bone screw 14b relative to the second end cup 1220, preventing pivotal rotation of the axis of elongation of the bone screw 14b relative to the orthopaedic device 1200.

Figure 13A:
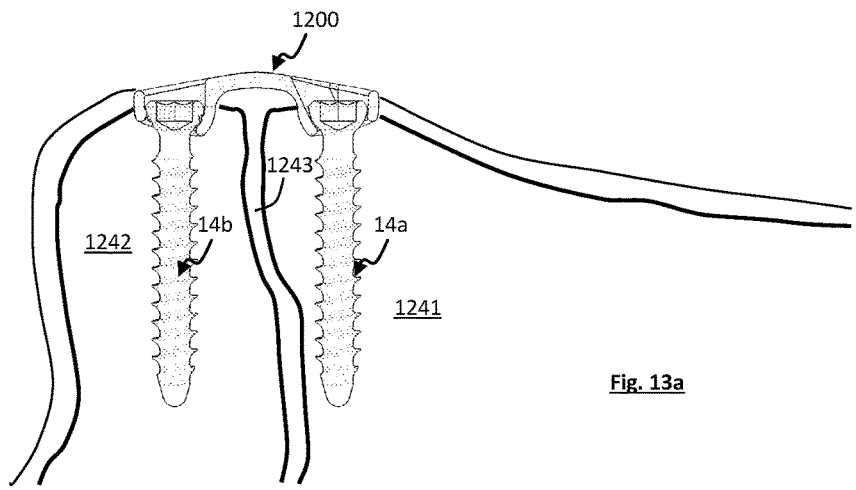
FIGS. 13a and 13b illustrate rotation of bone screws used with the orthopaedic devices of FIGS. 12a and 12b when implanted at a bone.
Figure 13B:
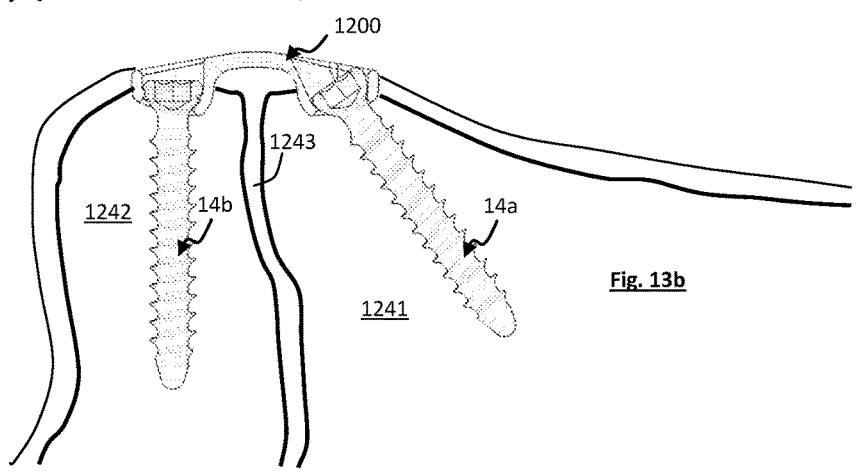

FIGS. 13a and 13b provide illustrative examples of how the first and second bone screws 14a, 14b, when used in conjunction with the orthopaedic device 1200, are positioned before and after bone growth, respectively. As can be seen from FIG. 13b, after bone growth the first bone screw 14a that is located in a first bone region, specifically the metaphysis 1241, has rotated (pivoted) relative to the orthopaedic device 1200. In contrast, the second bone screw 14b, located in a second bone region, specifically the epiphysis 1242, has remained in a substantially fixed position relative to the orthopaedic device 1200 and also relative to the growth plate 1243 located between the metaphysis 1241 and the epiphysis 1242.

Figure 14:
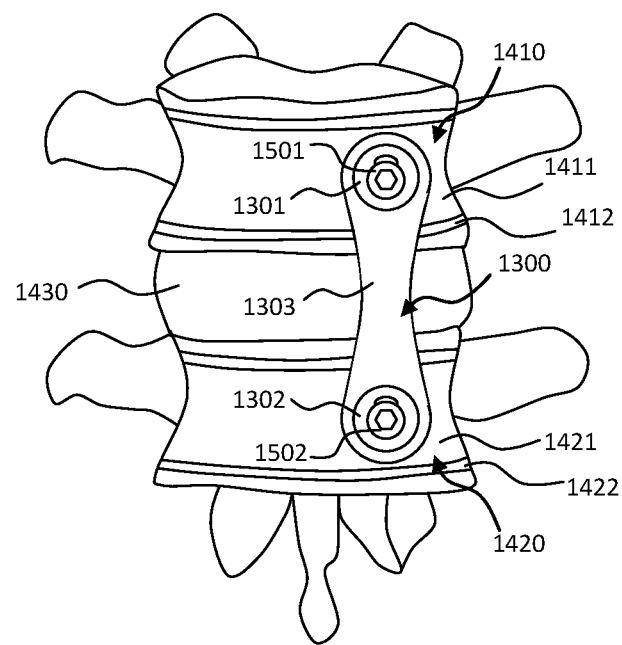
FIG. 14 shows an anterior view of an orthopaedic device according to another embodiment of the present disclosure implanted at a portion of a spine.

Various orthopaedic devices discussed above are illustrated in the Figures implanted at the end of a long bone, where first and second bone regions are provided separated by a growth plate. Thus, the first and second bone regions are part of the same bone. However, orthopaedic devices according to the present disclosure need not necessarily be used in conjunction with a long bone or the same bone only. For example, the first and second bone regions may be part of one or more irregular bones such as vertebrae of the spine, and, referring to FIG. 14, in one embodiment, the first bone region 1411 is part of a first vertebra 1410 and the second bone region 1421 is part of a second vertebra 1420 adjacent the first vertebra 1410. An orthopaedic device 1300 is provided having first and second end cups 1301, 1302 countersunk in recesses of the first and second bone regions in a similar arrangement to the orthopaedic device 10 of FIGS. 1a to 1e. The first end cup 1301 is fixed using a first bone screw 1501 to the first vertebra 1410 and the second end cup 1302 is fixed to the second vertebra 1420 using a second bone screw 1502. The connection portion 1303 of the device 1300 extends across portions of the outer surfaces of the first and second vertebrae 1410, 1420 including across two growth plates 1412, 1422, one from each of the vertebrae 1410, 1420. The connection portion 1303 also extends across the vertebral disc space including the vertebral disc 1430 between the first and second vertebrae 1410, 1420. Thus, the orthopaedic device 1300 can provide for guided growth of the spine, while retaining a low profile at the spine. The profile may be such that the device does not rub on vital intrathoracic or intra-abdominal or retroperitoneal structures. To insert the device, open surgery may be carried out or the device may be inserted thorascopically, for example.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An orthopaedic system for fixing between first and second regions of bone separated by a growth plate, comprising:
   a bone screw having a threaded shaft and a head; and
   a device including a first end portion configured to fix to the first bone region; a second end portion configured to fix to the second bone region; and a connection portion connected between the first and second end portions and having an underside to extend across an outer surface of the bone that includes the growth plate between the first and second bone regions, wherein the first end portion includes a first open cup that protrudes relative to the connection portion such that it defines an unthreaded interior space, wherein the unthreaded interior space is at least partly receivable in a first recess in the first bone region and is configured to receive therein at least a portion of the head of said bone screw, wherein the second end portion includes a second open cup that protrudes relative to the connection portion such that it is at least partly receivable in a second recess in the second bone region, and wherein the first open cup defines a first opening configured to receive the threaded shaft for fixing said device to the first bone region, the first open cup permitting pivotal rotation of at least a portion of said head of said bone screw relative to said device within said first recess in said first bone region.

2. The device of claim 1, wherein the connection portion has an inner surface configured to face in an inwards direction towards an outer surface of the bone, and wherein the first end portion protrudes in the inwards direction.

3. The device of claim 2, wherein a first shoulder region is formed at an interface between an inner surface of the first end portion and the inner surface of the connection portion.

4. The device of claim 3, wherein the first shoulder region defines an angle of at least 90 degrees.

5. The device of claim 1, wherein the first and second end portions are rigid and the connection portion is non-rigid.

6. The device of claim 5, wherein the connection portion comprises a flexible link.

7. The device of claim 6, wherein the flexible link is a flexible tape or band.

8. The device of claim 7, wherein the first and second end portions comprise slots and the flexible link connects to the first and second end portions by extending into the slots.

9. A method of guiding growth of a bone with an orthopaedic device having a first end portion defining a protrusion, a second end portion defining a second protrusion, and a connection portion connected between the first end portion and the second end portion, the bone including first and second regions of bone separated by a growth plate, the method comprising:

Locating the first protrusion of the orthopaedic device in a first recess in the first bone region;

Locating the second protrusion of the orthopaedic device in a second recess in the second bone region;

extending a shaft extending from a head of the first fixation device from the first protrusion into the first bone region;

pivotally locating at least a portion of the head of the first fixation device in the first protrusion;

extending a shaft extending from a head of the second fixation device from the second protrusion into the second bone region; and locking at least a portion of the head of the second fixation device in the second protrusion.

10. The method of claim 9, comprising locating the second end portion in a second recess at the second bone region, wherein the second end portion protrudes relative to the connection portion.

11. An orthopaedic device for fixing between first and second regions of bone separated by a growth plate, the orthopaedic device comprising:

a first end portion to fix to the first bone region;
a second end portion to fix to the second bone region; and
a connection portion connected along an axis between the first and second end portions to extend across an outer surface of the bone between the first and second bone regions, wherein the first end portion defines a first protrusion configured to receive at least a portion of a head of a first fixation device therein and pass a shaft of the first fixation device therethrough to fix the orthopaedic device to the first bone region;

wherein the second end portion defines a second protrusion configured to receive at least a portion of a head of a second fixation device therein and pass a shaft of the second fixation device therethrough to fix the orthopaedic device to the second bone region;

wherein the first end portion is configured to allow pivotal rotation of the first fixation device relative to the orthopaedic device when the head of the first fixation device is received in the first protrusion;

wherein the second end portion is-adapted and configured to restrict pivotal rotation of the second fixation device relative to the orthopaedic device when the head of the second fixation device is received in the second protrusion; and wherein each of the first protrusion and the second protrusion are deeper along the axis towards the center of the orthopaedic device and shallower along the axis away from the center of the of the orthopaedic device.

12. The orthopaedic device of claim 11, wherein the second protrusion is threaded and the head of the second fixation device is threadably received by the second protrusion.

13. The orthopaedic device of claim 12, wherein the first protrusion is not threaded.

14. The orthopaedic device of claim 12, wherein either the second protrusion or the head of the second fixation device includes locking threads.

15. The orthopaedic device of claim 12, wherein the second fixation device is a bone screw having a threaded head.

16. The orthopaedic system of claim 1, wherein the device has an axis of elongation between the first and second cups, and each of the first cup and the second cups are deeper along the axis towards the center of the orthopaedic device and shallower along the axis away from the center of the of the orthopaedic device.

17. The orthopaedic system of claim 16 wherein the second open cup includes threads.

18. The orthopaedic system of claim 16, wherein the first opening is elongated along the axis.

19. The method of claim 9, wherein the first end portion has a first cup shape with the bottom of the first cup shape being configured to be received with the first recess, and the second end portion has a second cup shape with the bottom of the second cup shape being configured to be received with the first recess.

20. The method of claim 19, wherein the first fixation device has an end, and the first cup shape is configured such that the end of the fixation device does not protrude from the top surface of the first cup shape.

21. The method of claim 19, wherein the first cup shape includes cylindrical sidewalls.

22. The method of claim 19, wherein the first fixation device is a first bone screw having a first axis and the second fixation device is a second bone screw having a second axis.

23. The method of claim 22, wherein the first fixation device has a first axis and the second fixation device has a second axis, and the fixed first fixation device is parallel to the fixed second fixation device.

24. The device of claim 1, wherein the unthreaded interior space is configured to receive therein all of the head of said bone screw.

25. The device of claim 24, wherein the connection portion has an inner surface configured to face in an inwards direction towards an outer surface of the bone, and wherein the first end portion protrudes in the inwards direction.

26. The device of claim 25, wherein a first shoulder region is formed at an interface between an inner surface of the first end portion and the inner surface of the connection portion.

27. The device of claim 26, wherein the first shoulder region defines an angle of at least 90 degrees.

28. The device of claim 24, wherein the first and second end portions are rigid and the connection portion is non-rigid.

29. The device of claim 28, wherein the connection portion comprises a flexible link.

30. The device of claim 29, wherein the flexible link is a flexible tape or band.

31. The method of claim 9, wherein locking the head of the second fixation device in the second protrusion includes threadedly engaging the head of the second fixation device with the second protrusion.

32. The method of claim 31, further comprising threadedly engaging the head of the second fixation device with the second protrusion concurrently with extending the shaft extending from the head of the second fixation device from the second protrusion into the second bone region.

33. The device of claim 13, wherein the first protrusion is configured to receive all of the head of the first fixation device therein, and wherein the second protrusion is configured to receive all of the head of the second fixation device therein.

34. The device of claim 14, wherein the first protrusion is configured to receive all of the head of the first fixation device therein, and wherein the second protrusion is configured to receive all of the head of the second fixation device therein.

35. The device of claim 15, wherein the first protrusion is configured to receive all of the head of the first fixation device therein, and wherein the second protrusion is configured to receive all of the head of the second fixation device therein.

* * * * *